United States Patent [19]
Crossley et al.

[11] Patent Number: 5,821,251
[45] Date of Patent: Oct. 13, 1998

[54] NITROGEN HETEROCYCLES

[75] Inventors: Roger Crossley, Reading; Albert Opalko, Maidenhead; Peter Jonathan Meade, Maidenhead; Barry John Langham, Reading, all of England

[73] Assignee: John Wyeth & Brother Limited, Taplow, England

[21] Appl. No.: 448,452

[22] PCT Filed: Feb. 10, 1995

[86] PCT No.: PCT/GB95/00279

§ 371 Date: Apr. 10, 1996

§ 102(e) Date: Apr. 10, 1996

[87] PCT Pub. No.: WO95/21823

PCT Pub. Date: Aug. 17, 1995

[30] Foreign Application Priority Data

Feb. 10, 1994 [GB] United Kingdom ............... 9402561
Dec. 15, 1994 [GB] United Kingdom ............... 9425344

[51] Int. Cl.$^6$ .................. A01N 43/42; C07D 215/16; C07D 215/00; C07D 401/00
[52] U.S. Cl. .................. 514/311; 546/153; 546/156; 546/164; 546/167; 546/159
[58] Field of Search .................. 546/164, 167, 546/153, 156, 159; 514/311

[56] References Cited

U.S. PATENT DOCUMENTS 4,576,949  3/1986  Smith ............................ 514/277
5,110,815  5/1992  Effland .......................... 514/228.2

FOREIGN PATENT DOCUMENTS 1432378  4/1976  United Kingdom ......... C07D 215/16
1463666  2/1977  United Kingdom ......... C07D 221/16
9218482  10/1992  WIPO .

OTHER PUBLICATIONS

Zimmerman and Zeng, J. Org. Chem. 55(16), 4789–91 (1990).
Bennett and Minor, J. Het. Chem. 16(4), 633–35 (1990).
Albrecht and Shröder, Arch. Pharm (Weinheim) 308(8), 588–94 (1975).
Zymalkowski and Kothari, Arch. Pharm (Weinheim) 303 (8), 667–75 (1970).
Reimann and Friesinger, Arch Pharm. (Weinheim), 318, 1105–1115 (1985).

Primary Examiner—Mukund J. Shah
Assistant Examiner—Tamthom T. Ngo
Attorney, Agent, or Firm—R. F. Boswell, Jr.

[57] ABSTRACT

This invention concerns a compounds of generic formula:

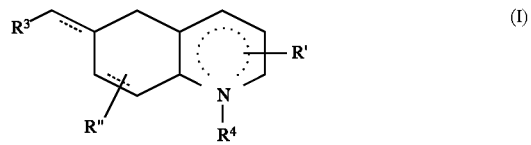

or a pharmaceutically acceptable salt thereof, where the dotted lines represent optional bonds with the nitrogen ring optional bonds being between one adjacent pair on ring atoms, $R^3$ is an optionally substituted $C_6$–$C_{10}$ aryl or heteroaryl group; said aryl or heteroaryl radicals being optionally substituted by one or more substituents the same or different, $R^4$ represents hydrogen, or a group of formula —$CR^aR^bR^c$ where $R^a$, $R^b$ and $R^c$ are independently selected from hydrogen, $C_1$–$C_6$ alkyl, optionally substituted $C_6$–$C_{10}$ aryl, optionally substituted heteroaryl, $C_1$–$C_6$ alkyl substituted by optionally substituted $C_6$–$C_{10}$ aryl or heteroaryl, R' represents one or more optional substituents the same or different, selected from one or more of the following: halogen, $C_1$–$C_6$ alkyl, $C_2$–$C_7$ alkoxycarbonyl, $C_1$–$C_6$ hydroxyalkyl, CN, aminocarbonyl, $C_2$–$C_7$ alkanoyloxy ($C_1$–$C_6$)alkyl, carboxy, $C_2$–$C_7$ alkanoxyamino, optionally substituted $C_6$–$C_{10}$ or heteroaryl or an optionally substituted ($C_6$–$C_{10}$ aryl)alkyl or a heteroaryl alkyl radical; said aryl or heteroaryl radicals being optionally substituted by one or more substituents the same or different, and R" represents one or more optional mono- or di- valent substituents in the 5, 7 or 8 positions the same or different: monovalent substituents being selected from the following: $C_1$–$C_6$ alkyl, $C_2$–$C_7$ alkanoyloxy, hydroxy, amino, $C_2$–$C_7$ alkanoylamino, $C_1$–$C_6$alkylamino, $C_1$–$C_6$ hydroxalkyl, R" can also represent hydroxy in the 6 position (when the optional bond is absent); the di-valent substituents being selected from oxo (i.e=O) and methylene (i.e =$CH_2$).

which compounds have pharmaceutical uses conferred by their ability to block voltage gated potassium channels.

19 Claims, No Drawings

NITROGEN HETEROCYCLES

This is a 371 application of PCT/GB95/00279 filed on Feb. 10, 1995.

This invention relates to nitrogen heterocycles, more particularly to substituted quinolines, partially or totally saturated, to processes for preparing them, to pharmaceutical compositions containing them. The compounds have pharmaceutical uses conferred by their ability to block voltage gated potassium channels.

Voltage gated potassium ion ($K^+$) channels which produce transient outward currents (TOC) are present in the cell membranes of neurones and serve to repolarise the cell following a depolarisation by opening and allowing potassium ions to flow from the inside of the cell to the outside. They are, therefore, one of the main regulating influences on the nerve cell firing and determine the amount of current reaching the terminal regions of the cells. This in turn regulates the amount of neurotransmitter substances released from the nerve terminals. In addition, they help to determine the refractory period of the nerve cell and hence the probability of the cell firing again within a certain time. This governs neuronal excitability and also the tendency of a cell to undergo repetitive firing. An ability to modify the functioning of these channels by chemical means is likely to produce therapeutically useful agents. So far the agents which are known to block the TOC channels are toxins such as the snake toxin dendrotoxin, or 4-aminopyridine and its derivatives. Blockade of the TOC channels leads to a change in the pattern of transmitter release and depending upon the pattern and type of neurone affected different therapeutic ends will result. For example TOC blockers which increase dopaminergic transmission in the substantia nigra will be of use in treatment of Parkinson's disease. Likewise, an increase in cholinergic function is of use in Alzheimer's disease and in cognition enhancement. Because of the complicated neural networks in the brain blockade of the TOC may also lead to increase in more than one transmitter substance at a time and this can act synergistically where a disease state is associated with more than one transmitter deficit as is often the case. It is evident, therefore that TOC blockers may be of use in areas of depression, pain, psychoses, cognition, memory and learning, anxiety, Parkinson's disease and Alzheimer's disease. In addition they can be used as a treatment for conditions where there is an impairment of nerve transmission such as multiple sclerosis.

Compounds which act to increase channel function may be termed channel openers and these serve to increase the braking action of the channels on the cells. In this respect they will also reduce the likelihood of the cells to undergo repetitive firing and may be used as anticonvulsants in the treatment of epilepsy. Also, their action to reduce neurotransmitter release means that they may be used as anaesthetics, analgesics, sedatives and anxiolytics.

This invention provides compounds of generic formula (I):

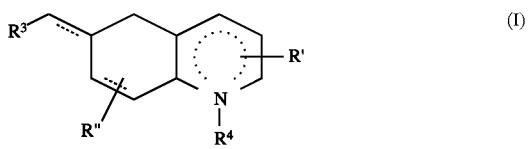

or a pharmaceutically acceptable salt thereof, where the dotted lines represent optional bonds with the nitrogen ring optional bonds being between one adjacent pair of ring atoms, $R^3$ is an optionally substituted $C_6$–$C_{10}$ aryl or heteroaryl group; said heteroaryl group containing 5 to 10 ring atoms of which one or more (e.g up to 3) of said atoms are heteroatoms selected from oxygen, nitrogen and sulphur, the same or different; said aryl or heteroaryl radicals being optionally substituted by one or more substituents the same or different, eg substituents commonly used in pharmaceutical chemistry such as for example: $C_1$–$C_6$ alkyl; $C_1$–$C_6$ alkoxy or such groups substituted by $C_6$–$C_{10}$ aryl or heteroaryl as defined above; halogen; halo $C_1$–$C_6$ alkyl; halo $C_1$–$C_6$ alkoxy; carboxy; hydroxy($C_1$–$C_6$)alkyl; ($C_1$–$C_6$alkoxy)carbonyl; amino including substituted amino, e.g mono- or di- ($C_1$–$C_6$ alkyl)-amino; nitro; hydroxy; mercapto; $C_1$–$C_6$alkylthio; ($C_1$–$C_6$)alkyl carbonyl; ($C_6$–$C_{10}$ aryl)carbonyl; ($C_2$–$C_7$)alkanoyloxy; ($C_7$–$C_{11}$)aroyloxy; ($C_1$–$C_6$)alkylcarbonylamino, ($C_6$–$C_{10}$aryl)carbonylamino; ($C_2$–$C_7$) alkoxycarbonylamino; $C_6$–$C_{10}$ aryl; heteroaryl as defined above; or $C_1$–$C_2$ alkylenedioxy;

$R^4$ represents hydrogen, or a group of formula —$CR^aR^bR^c$ where $R^a$, $R^b$ and $R^c$ are independently selected from hydrogen, $C_1$–$C_6$ alkyl, optionally substituted $C_6$–$C_{10}$ aryl, optionally substituted heteroaryl, $C_1$–$C_6$ alkyl substituted by optionally substituted $C_6$–$C_{10}$ aryl or heteroaryl in which the substituent(s) is/are for example as illustrated above in connection with $R^3$;

R' represents one or more optional substituents the same or different, selected from one or more of the following: halogen, $C_1$–$C_6$ alkyl, $C_2$–$C_7$ alkoxycarbonyl, $C_1$–$C_6$ hydroxyalkyl, CN, aminocarbonyl, $C_2$–$C_7$ alkanoyloxy ($C_1$–$C_6$)alkyl, carboxy, $C_2$–$C_7$ alkanoxylamino, optionally substituted $C_6$–$C_{10}$ or heteroaryl or an optionally substituted ($C_6$–$C_{10}$ aryl)alkyl or a heteroaryl alkyl radical; said heteroaryl group containing 5 to 10 ring atoms of which one or more (e.g up to 3) of said atoms are heteroatoms selected from oxygen, nitrogen and sulphur, the same or different; said aryl or heteroaryl radicals being optionally substituted by one or more substituents the same or different, eg substituents commonly used in pharmaceutical chemistry such as for example: $C_1$–$C_6$ alkyl, $C_1$–$C_6$ alkoxy, or such groups substituted by $C_6$–$C_{10}$ aryl or heteroaryl as defined above; halogen; halo $C_1$–$C_6$ alkyl, halo $C_1$–$C_6$ alkoxy; carboxy; hydroxy ($C_1$–$C_6$)alkyl $C_2$–$C_7$ alkanoyloxy($C_1$–$C_6$)alkyl; ($C_1$–$C_6$alkoxy)carbonyl; amino including substituted amino, e.g mono- or di- ($C_1$–$C_6$ alkyl)-amino; nitro; hydroxy; mercapto; $C_1$–$C_6$alkylthio; ($C_1$–$C_6$alkyl) carbonyl; ($C_6$–$C_{10}$ aryl)carbonyl; ($C_2$–$C_7$)alkanoyloxy; ($C_7$–$C_{11}$)aroyloxy; ($C_1$–$C_6$alkyl)carbonylamino, ($C_6$–$C_{10}$aryl)carbonylamino; ($C_2$–$C_7$ alkoxycarbonyl) amino; $C_6$–$C_{10}$ aryl; heteroaryl as defined above; or $C_1$–$C_2$ alkylenedioxy; and R" represents one or more optional mono- or di- valent substituents in the 5, 7 or 8 positions the same or different: monovalent substituents being selected from the following:$C_1$–$C_6$ alkyl, $C_2$–$C_7$ alkanoyloxy, hydroxy, amino, $C_2$–$C_7$ alkanoylamino, $C_1$–$C_6$alkylamino, $C_1$–$C_6$ hydroxalkyl, R" can also represent hydroxy in the 6 position (when the optional bond is absent); the di-valent substituents being selected from oxo (i.e=O) and methylene (i.e =$CH_2$).

In a subgeneric aspect this invention provides compounds of formula IA:

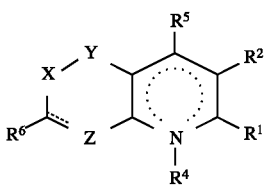

(IA)

or a pharmaceutically acceptable salt thereof,
wherein the dotted lines represent optional bonds with the nitrogen ring optional bond being between any adjacent ring atoms in the 3, 4; 4, 4a; or 4a, 8a positions;
wherein $R^1$ is H, or a $C_1$–$C_6$ alkyl, optionally substituted $C_6$–$C_{10}$ or heteroaryl or an optionally substituted ($C_6$–$C_{10}$ aryl)alkyl or a heteroarylalkyl radical; said heteroaryl group containing 5 to 10 ring atoms of which one or more (e.g up to 3) of said atoms are heteroatoms selected from oxygen, nitrogen and sulphur, the same or different; said aryl or heteroaryl radicals being optionally substituted by one or more substituents the same or different, eg substituents commonly used in pharmaceuticals chemistry such as for example: $C_1$–$C_6$ alkyl, $C_1$–$C_6$ alkoxy, or such groups substituted by $C_6$–$C_{10}$ aryl or heteroaryl as defined above; halogen; halo $C_1$–$C_6$ alkyl; halo $C_1$–$C_6$ alkoxy; carboxy; hydroxy($C_1$–$C_6$)alkyl; ($C_1$–$C_6$alkoxy)carbonyl; amino including substituted amino, e.g mono- or di- ($C_1$–$C_6$ alkyl)-amino; nitro; hydroxy; mercapto; $C_1$–$C_6$alkylthio; ($C_1$–$C_6$alkyl) carbonyl; ($C_6$–$C_{10}$ aryl) carbonyl; ($C_2$–$C_7$)alkanoyloxy; ($C_7$–$C_{11}$)aroyloxy, ($C_1$–$C_6$alkyl)carbonylamino, ($C_6$–$C_{10}$aryl) carbonylamino; ($C_2$–$C_7$) alkoxycarbonylamino; $C_6$–$C_{10}$ aryl; or heteroaryl as defined above;
wherein $R^2$ is hydrogen, $C_1$–$C_6$ alkyl, $C_1$–$C_6$ hydroxyalkyl, $C_2$–$C_7$ alkanoyloxy($C_1$–$C_6$)alkyl, $C_2$–$C_7$ alkoxycarbonyl, cyano, aminocarbonyl, carboxy or $C_2$–$C_7$ alkanoylamino;
X is a group of formula

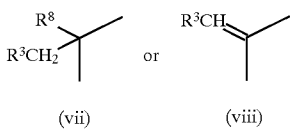

where $R^8$ is H or OH;
$R^3$ is a $C_6$–$C_{10}$ aryl or a heteroaryl radical containing 5 to 10 ring atoms of which one or more (e.g up to 3) of said atoms are heteroatoms selected from oxygen, nitrogen and sulphur, the same or different; said aryl or heteroaryl radical being optionally substituted by one or more substituents the same or different as defined above in the definition of $R^1$;
Y is

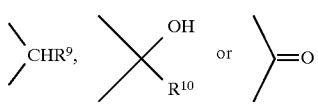

where $R^9$ represents hydrogen, $C_1$–$C_6$ alkyl, $C_2$–$C_7$ alkanoyloxy, optionally substituted heteroaryl, optionally substituted $C_6$–$C_{10}$ aryl or $CH_2OH$; and $R^{10}$ represents hydrogen or $C_1$–$C_6$ alkyl;
and $R^4$ represents hydrogen, or a group of formula —$CR^aR^bR^c$ where $R^a$, $R^b$ and $R^c$ are independently selected from hydrogen, $C_1$–$C_6$ alkyl, optionally substituted $C_6$–$C_{10}$ aryl, optionally substituted heteroaryl, $C_1$–$C_6$ alkyl substituted by optionally substituted $C_6$–$C_{10}$ aryl or heteroaryl in which the substituent(s) is/are for example as illustrated above in connection with $R^1$;
Z is C=O, C=$CH_2$, —$CHR^7$— or =$C(R^7)$— where $R^7$ is hydrogen, OH, $CH_2OH$, $NH_2$, $C_2$–$C_7$ alkanoyloxy, $C_2$–$C_7$ alkanoylamino $C_1$–$C_6$alkylamino or a $C_1$–$C_6$ alkyl group optionally substituted by a group $R^3$ as defined above;
$R^5$ is hydrogen, $C_1$–$C_6$ alkyl, $C_6$–$C_{10}$ aryl, heteroaryl or a $C_1$–$C_6$alkyl substituted by $C_6$–$C_{10}$ aryl or heteroaryl; said aryl or heteroaryl groups being optionally substituted as defined for $R^1$ above; and
$R^6$ is $NH_2$, $C_7$–$C_{17}$ aralkanoylamino, $C_2$–$C_7$ alkanoylamino or $R^6$ is one of the values listed for $R^5$ above.

In all the formulae above, examples of alkyl as a group or part of a group, e.g aralkyl, alkanoyl, are straight or branched chain groups of up to 6 carbon atoms especially of 1 to 4 carbon atoms such as methyl, ethyl, n-propyl, isopropyl, n-butyl and sec butyl. Examples of "alkoxy" as a group or part of a group, e.g alkoxycarbonyl, are groups of formula alkyl-O- where alkyl has the meanings immediately above. Examples of aryl as a group or part of a group, e.g aralkyl, aralkanoyl, are mono- or bicyclic groups of 6 to 10 carbon atoms such as phenyl and naphthyl, e.g 1 or 2-naphthyl. Heteroaryl groups have heteroatoms selected from oxygen, nitrogen and/or sulphur. Examples of heteroaryl as a group or part of a group, e.g heteroarylalkyl, are mono- or bicyclic groups of 5 to 10 ring atoms such as those having one nitrogen heteroatom e.g 2 or 3-pyrrolyl, 2, 3 or 4-pyridyl, quinolyl (e.g 2, 3 or 6-quinolyl) isoquinolyl (e.g 1-, 3- or 6-isoquinolyl); one sulphur atom, e.g 2- or 3-thienyl or benzothienyl (e.g 2, 3 or 6-benzothienyl); or one oxygen atom, e.g 2- or 3-furanyl or benzofuranyl (e.g 2-, 3- or 6-benzofuranyl); or two or more heteroatoms e.g thiazolyl (e.g 2-thiazolyl), imidazolyl (e.g 2-imidazolyl); oxazolyl (e.g 2-oxazolyl).

Examples of optional substituents are alkyl, alkoxy, aryl and heteroaryl as illustrated above, chlorine, bromine, fluorine, $CF_3$, $CH_2F$, $CF_3CH_2$, $HOCH_2$—, HOCH(Me)—, HO($CH_2$)$_2$—, MeOOC—, EtOOC—, $NH_2$, NHMe—, NHEt—, $NMe_2$—, $NO_2$, HO, HS—, MeS—, EtS—, $CH_3CO$—, EtCO—, PhCO—, $CH_3CONH$—, EtCONH—, PhCONH—, MeOOCNH—, EtOOCNH—, $CH_3CO.O$—, EtCO.O— or methylene- or ethylene-dioxy.

Examples or $R^1$ are hydrogen, methyl, phenyl, benzyl, chlorine and bromine.

The group $R^2$ may be for example hydrogen, methyl, —COOMe, —COOEt or —$CH_2OH$.

$R^3$ may be for example phenyl or phenyl substituted by one or more substituents as illustrated above, e.g substituents the same or different selected from: $C_1$–$C_6$ alkoxy such as methoxy, ethoxy; halogen such as chlorine or bromine; $CF_3$; $CF_3O$; $C_1$–$C_6$ alkyl such as methyl or ethyl; hydroxy; cyano and carboxy. Preferred values for $R^3$ are methoxyphenyl, e.g 4-methoxyphenyl and hydroxyphenyl, e.g 4-hydroxyphenyl.

Examples of the group Y are $CH_2$, CO, C=$CH_2$, CHOH or CHOCOCH$_3$, (i.e in formula I, R" is absent, =O, =$CH_2$, OH or OCOCH$_3$ respectively).

The value of $R^4$ is for example hydrogen or a group of formula —$CR^aR^bR^c$ where $R^a$ and $R^b$ are independently selected from hydrogen, methyl, ethyl, propyl, isopropyl or butyl and $R^c$ is selected from hydrogen, methyl, ethyl, isopropyl, propyl, butyl or a $C_6$–$C_{10}$ aryl or a heteroaryl group containing 5–10 ring atoms of which one or more of said atoms are heteroatoms selected from oxygen, nitrogen and sulphur in which said aryl and heteroaryl moieties are optionally substituted as illustrated above.

Preferably $R^a$ is hydrogen, $R^b$ is methyl and $R^c$ is optionally substituted aryl such as phenyl or substituted phenyl such as illustrated above.

The group Z may be for example C=O, C=CH$_2$, —CH$_2$—, —CH(Me); —CH(Ph)—, =CH(Me)— or —CH(CH$_2$Ph)—, (i.e in formula I, R" represents =O, =CH$_2$, absent, Me, Ph, Me or CH$_2$Ph).

Examples of $R^5$ are hydrogen, $C_1$–$C_4$ alkyl, e.g methyl, phenyl, benzyl and substituted phenyl where substituents are as defined hereinabove.

Examples of $R^6$ are hydrogen, NH$_2$ and NHCOCH$_3$.

Preferred compounds of formula I and IA have $R^3$ represents 4-methoxyphenyl. Also preferred are compounds where $R^2$ represents methyl or hydrogen.

Included in the scope of this invention as defined under formula I are the following compounds:

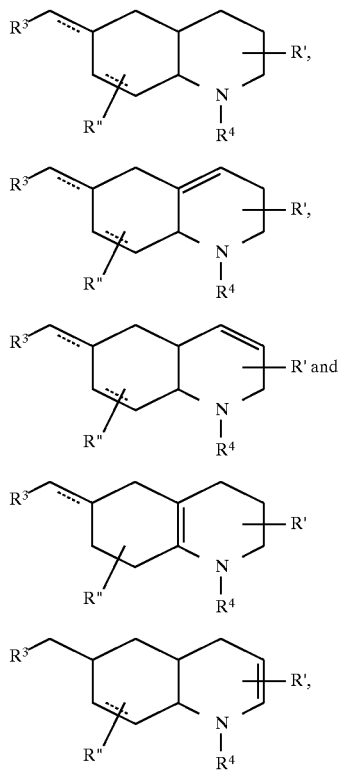

Particularly preferred are compounds of formula (K):

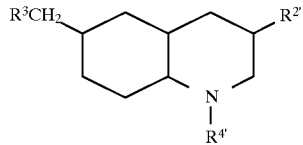

in which formulae $R^{2'}$ is hydrogen, $C_1$–$C_6$ alkyl, $C_2$–$C_7$ alkoxycarbonyl, acetylamino, CN or CH$_2$OH; $R^3$ is as defined above, preferably unsubstituted or substituted phenyl, e.g where the substituents is/are selected from $C_1$–$C_6$ alkyl, $C_1$–$C_6$ alkoxy, hydroxy, halogen and methylene or ethylene-dioxy; and $R^{4'}$ is hydrogen, alkyl or optionally substituted aryl($C_1$–$C_6$) alkyl in which the alkyl group is itself optionally substituted by $C_1$–$C_6$ alkyl.

Examples of $R^{4'}$ include phenylmethyl or α-methylphenylmethyl in which the phenyl group is optionally substituted by substituents as listed above.

Preferred values of $R^{4'}$ are PhCH(Me)—; PhCH$_2$— and H.

The compounds of formula I (including subgeneric formulae IA and K) possess one or more (e.g four, five or six) asymmetric centres and accordingly the compounds may exist and be isolated in a number of optically active stereoisomeric forms. When X has formula viii then geometric isomers (E,Z) are also obtained. This invention encompasses the compounds of formula I in any optically active or geometric form or mixtures thereof eg, racemates or diastereoisomers. Standard separation techniques may be used to isolate particular enantiomeric and diastereomeric forms. For example a racemic mixture may be converted to a mixture of optically active diastereoisomers by reaction with a single enantiomer of a 'resolving agent' (for example by diastereomeric salt formation or formation of a covalent bond). The resulting mixture of optically active diastereoisomers may be separated by standard techniques (e.g crystallisation or chromatography) and individual optically active diastereoisomers then treated to remove the 'resolving agent' thereby releasing the single enantiomer of the compound of the invention. Chiral chromatography (using a chiral support, eluent or ion pairing agent) may also be used to separate enantiomeric mixtures directly.

Stereospecific synthesis using optically active starting materials and/or chiral reagent catalyst and/or solvents may also be employed to prepare particular diastereoisomers or even a particular enantiomer.

For example where the compound of formula I is prepared by an addition process creating one or more optical centres then carrying out the reaction using a chiral catalyst or agent or in a chiral environment can give the product as a single enantiomer.

Compounds of formula I can have one asymmetric centre at the 6- position. Accordingly such compounds can be isolated as the R- or S- enantiomers or as the racemates. In the saturated or partially saturated systems, e.g octahydroquinolines or decahydroquinolines where the bridgehead carbons 4a and 8a are linked by a single bond, then two further chiral centres (4a and 8a) are present and the compounds can be isolated as the individual enantiomers. In addition position 3 may also be a chiral centre. When $R^4$ represents an aryl alkyl(alkyl)- or heteroarylalkyl(alkyl)-moiety then yet a further chiral centre is present. All such enantiomers and diasteresoisomers of the compounds of formula I are included in this invention.

The compounds of formula I possess pharmacological activity in particular they block voltage gated potassium channels. They may therefore by used to treat CNS disorders as described above such as depression, pain psychoses, anxiety, movement disorders (such as Parkinson's disease) and multiple sclerosis and in enhancing cognition, memory and learning. They demonstrate their ability to block voltage gated potassium channels in dorsal root ganglion cells by the following standard test procedures:

Procedure 1 Modulation of voltage-activated K$^+$ currents in dorsal root ganglion (DRG) cells:

The method used in the culture or dorsal root ganglion cells is similar to that described by Wood et. al., Capsaicin induced ion fluxes in dorsal root ganglion cells in culture, J. Neuroscience, 8, 3208–3220) (1988). Dorsal root ganglia are dissected mainly from around the lumbar and thoracic vertebrae and placed in a conical centrifuge tube containing Ham's F14 nutrient mixture (F14:Imperial Laboratories) plus horse serum (HS: GIBCO or Flow). When all ganglia have been collected (ex ca. 14 pups) the excess medium is removed and the ganglia incubated for 30 min in "F14+HS" containing 0.1% collagenase Type 1A-S (Sigma). Excess medium is removed, ganglia washed in 4 ml F14 (no HS), resuspended and spun down at 900 g for 10 s. The supernatant is again removed and replaced with 1.8 ml F14 (no HS) plus 0.2 ml trypsin (GIBCO) at a final concentration of 0.25%. The ganglia are then incubated at 37° C. for 30 min agitating every 10 min to prevent clumping. The trypsinisation is inhibited by the addition of 6 ml "F14+HS" and cells are resuspended and centrifuged as before. The medium is removed and 2 ml added of "F14+HS" containing 0.4% DNAase 1 (Sigma). The ganglia are then triturated gently 15–20× using a siliconised pasteur pipette, filtered through a 90 mm nylon mesh filter and collected into a centrifuge tube. The filter is further washed with 2 ml of "F14+HS" which is collected into the same tube. The suspension is spun at 900 g for 3 min, the supernatant removed and the cells resuspended in DRG Growth Medium (DRG-GM) which consists of: HAMS F14 nutrient mixture (40%, v/v), HS(10%, v/v) C6 conditioned medium (50%, v/v), penicillin/streptomycin (100 U/ml; 100 $\mu$g/ml) and NGF (30 $\mu$g/ml). Cells are then plated out onto five 60 mm poly-L-lysine-coated tissue culture petri dishes (see below).

Replating

After a few days in culture (3–7 days, usually), cells are resuspended from 60 mm dishes using a 0.25% solution of trypsin in F14. An equal volume of DRG-GM is added to inhibit the trypsin, the cells are spun at 900 g for 5 minutes and resuspended in 0.25–0.5 ml of DRG-GM. Neurites are removed by gentle trituration through a 21 g syringe needle (15–20 strokes) and a drop of the cell suspension is then placed on each of 5–6 poly-D-lysine- and laminin-coated 35 mm petri dishes (see below). After 30 minutes incubation at 37° C., each plate is flooded with ca 1.5 ml DRG-GM and after about 1 hour incubation, cells are ready for electrophysiological recording. This final step is carried out specifically in order to remove neurites which hinder good voltage-clamp of the cells.

Coating of plates:

2 ml of poly-D-lysine (Sigma), reconstituted in distilled water to 100 $\mu$g/ml, are added to each plate and left for 1–2 hours. Plates are then washed with water and left to dry. Laminin (5 $\mu$g/ml) is added as a drop to the centre of plates (previously coated with poly-D-Lys), left for 45 min before removal of excess and use of plates.

Electrophysiology:

Recordings are made using an AxoClamp-2A (Axon Instruments Inc) switiching clamp amplifier using patch electrodes (4–8 Mohms), made from borosilicate glass capillary tubes (GC150TF-10, Clark Electromedical) and fire-polished. Electrodes are filled with (in mM): 140 K Gluconate, 2 MgCl$_2$, 1.1 EGTA/KOH, 5 HEPES, 20 sucrose, 2 MgATP, 0.2 GTP; pH set to 7.2 with KOH and osmolarity adjusted with sucrose to 310 mOsm. The electrodes are then and dipped in Sigmacote (Sigma) prior to recording to reduce stray capacitance. The bathing solution in which cells are continually perfused (during recordings) consists of (in mM): 124 NaCl, 2.5 KCl, 4 MgCl$_2$, 5 HEPES, 10 glucose, 1 $\mu$M TTX, 20 sucrose pH set to 7•4 with NaOH and osmolarity adjusted with sucrose to 320 mOsm. Ca$^{2+}$ is omitted from the bathing medium in order to minimise voltage-activated Ca$^{2+}$ currents and Ca$^{2+}$ activated K$^+$ currents. TTX is included to block voltage-activated Na$^+$ currents, although in some recordings a residual TTX-resistant Na$^+$ current is evident. Recordings are made in voltage-clamp mode using a voltage-step protocol consisting of:

i) holding potential (V$_h$)=–30 mV (in order to inactivate transient outward current)

ii) 1 s prepulse to –100 mV iii) 1 s pulse to +60 mV to activate total outward current iv) return to –30 mV In some cases current-voltage(I-V) relationships are obtained in the presence and absence of test compound by constructing families of voltage steps over a range of membrane potentials (–100 mV to +60 mV) from a holding potential of either –30 mV or –100 mV. Voltage steps and data acquisition (current responses) are controlled by an Atari MegaSTE computer interfaced to the voltage-clamp via an ITC-16 ADC/DAC (Instrutech Corp.) and subsequent analysis carried out using REVIEW (Instrutech Corp). Test compounds are applied to individual neurones by a local microperfusion system, initially at a test concentration of 100 or 10 $\mu$M(solubility-permitting).

Calculations:

Current responses during the test voltage step to +60 mV (above) are measured off-line using REVIEW (Instrutech Corp). The following measurements are made:

peak (with ca. 50 ms) and Q integral (t=1 s) outward current measured at +60 mV:

i) after conditioning prepulse to –100 mV (includes non-inactivating as well as transient outward current (TOC)

ii) without conditioning prepulse (mainly non-inactivating current)

iii) difference (digital subtraction) of above currents corresponds to TOC).

Current amplitudes are obtained for: total outward current (K$_{-100}$), noninactivating current (K$_{-30}$) and TOC. Peak current amplitudes recorded in the presence of test compounds are expressed as a percentage of the corresponding control values.

Standard Compounds:

4-aminopyridine (100% block of TOC at 1 mM)

Toxin I (50% block of TOC at 100 nM)

(Toxin I is a dendrotoxin homologue.)

The compounds were also tested for blocking transient outward potassium currents (TOC) in the GH$_3$ rat pituitary cell line according to the procedure below:

Procedure 2:

GH$_3$ cells were obtained from either Flow Laboratories or European Centre for Animal Cell Cultures (Porton Down), and maintained in tissue culture using standard procedures and media for this cell line. Cells were plated on 35 mm plastic dishes and used subsequently for electophysiology with 1 to 10 days.

Currents were recorded using the whole-cell voltage clamp configuration of the patch clamp technique, using an Axopatch 1C amplifier (Axon Instruments). Patch electrodes were manufactured from aluminosilicate glass tubing (Clark Electomedical SM150F-10) and heat polished prior to use. Resistance was 1–5 M$\Omega$. No electrode coating was necessary for whole-cell recording. Signal acquisition and analysis was performed using pClamp software (Axon Instruments). A p-on-4 subtraction procedure was used to remove leak and capacitative currents on line. A holding potential of –100 mV was routinely used: this avoided accumulation of slow voltage-dependent inactivation.

Two main protocols were used in testing drugs. 1) Current-voltage (I-V) curves were collected, with incrementing steps of either 10 or 20 mV. Full I-V curves were obtained both in control and drug solutions. 2) a 'pharmacology' program, which involved single voltage steps fromm –100 to +60 mV, applied and collected at 20 s intervals. Compounds under investigation were applied via a 'U' tube rapid application system to a small area of the recording chamber. Drug applications were always bracketed by control solutions to ensure reversibility. The recording chamber was continously perfused at 1–5 ml.min$^{-1}$. Results are expressed at % of control peak current (step form −100 to +60 mV). However, where drugs have a time dependent effect on TOC, i.e acceleration of TOC decay, results are also expressed as a % of total charge transferred within a defined period of the voltage step from −100 to +60 mV.

The standard extracellular solution contained (in mM): NaCl 135 (or choline or TRIS chloride); KCl 5; MgCl$_2$ 4; EGTA 1; TEACl 10; HEPES 10; glucose 25; pH set to 7.4 with NaOH. TTX was usually at 100–200 nM.

The intracellular (pipette) solution was comprised of (in mM): K aspartate 120; KCl 20; MgCl$_2$ 1; cAMP 1; MgATP 2; EGTA 10; HEPES 10; pH 7.4 with KOH. Other intracellular substrates were often used without noticeable effect. This solution was stored in 1 ml aliquots at −4° C., and filtered at 0.2 μm.

These recording solutions precluded activation of voltage dependent Na, Ca, delayed rectifier and Ca-activated K currents. The resulting whole-cell currents chiefly comprised the transient outward potassium current, switching on with third power kinetics reaching peak amplitudes of ~1 nA at +60 mV, and a double exponential decay (time constants of ~30 and 160 ms at +60 mV). There is no significant change in current amplitude within the normal recording period, which may extend for up to 90 min. One dish of cells usually lasts several hours.

The standard compound 4-aminopyridine is a block @ 1–5 mM. (80% block at 5 mM).

RESULTS:

Results for representative compounds of this invention in the two abovementioned tests are shown in the Table below:

| COMPOUND EXAMPLE NO | CONCENTRATION | % Block of TOC | |
|---|---|---|---|
| | | PROCEDURE 1 DRG % | PROCEDURE 2 GH3 % |
| 1 | 100 μM | — | 55 |
| 2 | 100 μM | — | 31 |
| 3 | 100 μM | — | 68 |
| . | 10 μM | 32 | — |
| 4 | 100 μM | 60 | 56 |
| 6 | 10 μM | 29 | — |
| 8 | 10 μM | 49 | — |
| 9 | 10 μM | 28 | — |

The results show the ability of compounds of this invention to block voltage gated potassium channels in cells indicating pharmaceutical uses as described hereinabove.

This invention also provides processes for preparing the compounds of formula I and IA.

Many starting materials used herein can be derived from substituted catechols, reduced to give or form many known cyclohexane-1, 3- or -1,4-diones appropriately protected to give compounds of the type:

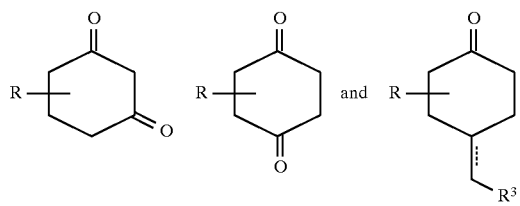

where R is R" or a group convertible thereto, and R$^3$ is is as defined herein. Such compounds can be converted to final products or other starting materials as described herein via known pyridine ring syntheses for example: Comprehensive Organic Chemistry, Vol. 4, Editor P G Sammes, Part 16.1, pages 3–84, Pyridines, by D M Smith, Pergamon Press; Comprehensive Heterocyclic Chemistry Vol. 2, Editors Boulton and McKillop Part 2A, "Six membered rings with one nitrogen atom", Pergamon Press and The Chemistry of Heterocyclic Compounds. Editor A Weissberger, Pyridine and Its Derivatives, Parts 1–4, (1962), Interscience Publishers.

Once a pyridine ring system is obtained it can be reduced, completely or partially as described in the literature to give saturated or partially saturated ring systems which themselves may be final products or starting materials.

Compounds of formula I are therefore useful for preparing other compounds of formula I as will be apparent from the processes described herein.

Compounds of formula I may be prepared by one of the following processes where if necessary reactive substituent groups are protected prior to reaction and removed thereafter; said processes comprising:

(A) reacting a compound of formula:

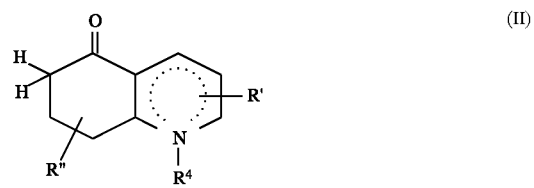

wherein the dotted lines, R', R" and R$^4$ are as defined herein with an aldehyde of formula R$^3$CHO, in the presence of base to give a corresponding compound of formula I which has oxo group in the 5-position and the optional bond to the 6-position is present, or (B) reacting a compound of formula:

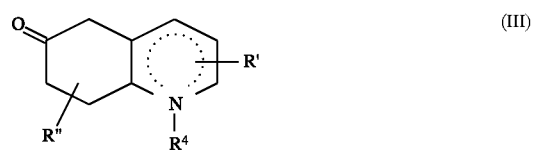

wherein R', R" and R$^4$ are as defined above with an anion of formula:

where R$^3$ is as defined above, e.g using a Grignard reagent, to give a corresponding compound of formula I having a 6-hydroxy group, which compound may be dehydrated to give a compound of formula I wherein the optional bond to the 6-position is present; or (C) reacting a compound of formula (III) as defined above with a Wittig reagent of formula:

(Ph)$_3$P=CHR$^3$ wherein R$^3$ is as defined above to give a corresponding compound of formula I where the optional bond to the 6-position is present; or (D) reacting a compound of formula (IV):

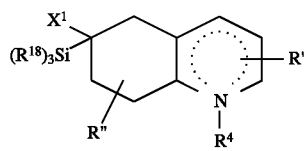

wherein R', R", and R$^4$ are as defined above, (R$^{18}$)3 is defined as three R$^{18}$ radicals the same or different selected from alkyl, cycloalkyl, aralkyl, aryl or electron donating substituents such as alkoxy, cycloalkoxy, aralkoxy, aryloxy, alkylthio, cycloalkythio, aralkylthio, arylthio, the group R$^d$R$^e$N— where R$^d$ and R$^e$ are selected from alkyl, cycloalkyl, aryl and aralkyl or R$^d$ and R$^e$ are joined to form a heterocyclic ring with the nitrogen atom to which they are attached (e.g. piperidinyl, pyrrolidinyl which may be substituted, e.g. by alkyl) and X$^1$ is sodium, potassium or lithium, with a compound of formula:

R$^3$CHO wherein R$^3$ is as defined above in connection with formula I; followed by treatment under acidic or basic conditions, to give a compound of formula I in which the optional bond to the 6-position is present;

or (E) reacting a compound of formula (III) as defined above with a compound of formula:

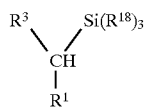

where R$^3$, R$^{18}$ and X$^1$ are as defined above, followed by treatment under acidic or basic conditions, or (F) converting a compound of formula I having at least one reactive substituent group or site to give a different compound of formula I;

or (G) reducing a tetrahydroquinoline compound of formula I (having three nitrogen ring double bonds) or a quaternary ammonium salt thereof to give a corresponding compound of formula I containing 2 or less (e.g. zero) nitrogen ring double bonds.

or (H) reducing a compound of formula (L):

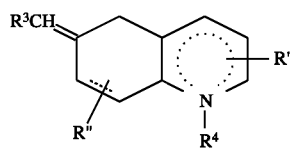

wherein R', R", R$^3$ and R$^4$ are as defined above, e.g. catalytically using 5% Pd/C and hydrogen, to give a compound of formula I wherein the optional bond to the 6-position is absent;

or (I) dehydrating a compound of formula (M):

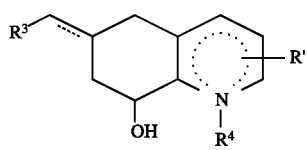

wherein the dotted lines R', R$^3$ and R$^4$ are as defined above, e.g. using polyphosphoric acid and warming, to give a compound of formula I having a double bond between the 7 and 8 positions, or (J) converting a basic compound of formula I to an acid addition or quaternary ammonium salt thereof, or vice versa, or (K) resolving a mixture of isomeric compounds of formula I to isolate a specific enantiomeric form substantially in the absence of other isomers.

Processes for preparing the subgeneric aspect of this invention, e.g. compounds of formula IA comprise one of the following:

a) reacting a compound of formula (IX):

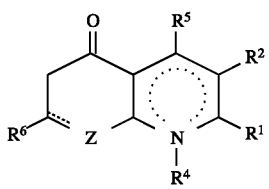

wherein the dotted lines, R$^1$, R$^2$, Z, R$^5$, R$^6$ and R$^4$ are as defined above, with an aldehyde of formula R$^3$ CHO, in the presence of base to give a corresponding compound of formula IA wherein X is formula (viii) and Y is C=O;

or (b) reacting a compound of formula (X):

$$\text{(X)}$$

wherein R$^1$, R$^2$ Z, R$^5$, R$^6$ and R$^4$ are as defined above, with an ylide of formula:

(Ph)$_3$P=CHR$^3$         (XI)

wherein R$^3$ is as defined above to give a corresponding compound of formula IA wherein X has formula (viii):

R$^3$CH=          (viii)

or c) reducing a compound of formula N:

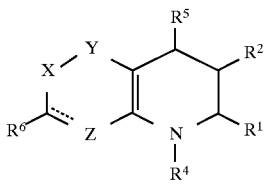

wherein $R^1$, $R^2$, X, Y, Z, $R^4$, $R^5$ and $R^6$ are as defined above and A also represents C=O to give a corresponding nitrogen ring saturated compound of formula IA, having a single bond between bridgehead carbons, of structure (O):

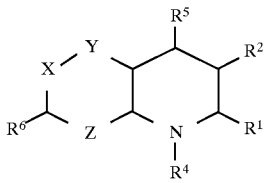

where A represents $CH_2$, or d) reducing a compound of formula XII:

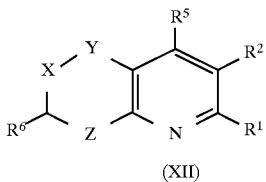

or a quaternary salt thereof wherein the dotted lines, $R^1$, $R^2$, X, Y, Z, $R^5$ and $R^6$ are as defined above to give a compound of formula IA wherein $R^4$ is hydrogen, or (e) converting any substituent group present in a compound of formula IA to another substituent group by known means; e.g. reducing $R^2$ is $(C_1-C_6$alkoxy$)$-carbonyl to give a compound of formula IA wherein $R^2$ is —$CH_2OH$ or f) reducing a compound of formula R is

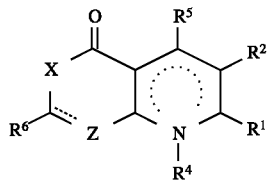

wherein the dotted lines, $R^1$, $R^2$, X, Z, $R^4$, $R^5$ and $R^6$ are as defined above, to give a corresponding compound of formula IA wherein Y is $CH_2$;

or g) reducing a compound of formula IA wherein X has formula (viii) to give a compound of formula IA wherein X has formula (vii) and $R^8$ is hydrogen; or h) hydrogenating a compound of formula IA where $R^4$ is a group of formula $CR^aR^bR^c$ wherein at least one of $R^a$, $R^b$ and $R^c$ is optionally substituted aryl to give a compound of formula IA wherein $R^4$ is hydrogen; or i) reducing a compound of formula

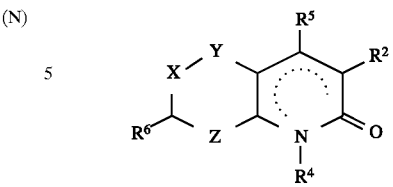

wherein X, Y, Z, $R^4$, $R^5$ and $R^6$ are as defined above to give a compound of formula IA where $R^2$ is hydrogen;

or j) resolving a mixture of isomeric compounds of formula IA using standard separation techniques to isolate a specific enantiomeric form in the absence of other isomers.

Methods for carrying out processes (A)–(K) and (a)–(j) are known in the literature and may be carried out by standard procedures. If required other sites in the molecule can be protected by known methods to avoid side reactions.

Processes a) and A) are conveniently carried out by heating in the presence of a small amount of organic base, e.g. piperidine.

Processes b) and C) may be carried out under Wittig reaction conditions using the desired substituted triphenylphosphonium halide. Processes for carrying out Wittig reactions are extensively described in the literature. See for example Org. React. 14, 270 (1965) and Org. Syn. Coll. Vol. 5 751 (1973).

Process B) may be carried out by reacting with a Grignard reagent of formula $R^3CH_2Mghal$ where hal is a halogen such as bromine.

Process (D) may be carried out under Peterson reaction conditions. In the process an intermediate of formula IV in which $X^1$ is $R^3CH(OX)$— (X is Li, Na or K) is formed and this compound is hydrolysed to the alcohol and dehydrated by acid or base treatment, removing any protection groups as required. Process (E) is analogous to Process (D) and may be carried under the same conditions.

Process c) may be conveniently carried out by chemical reduction for example using a trialkylsilane, e.g. triethylsilane, under acidic conditions (e.g. trifluoroacetic acid) and inert sovent e.g. dichloromethane to give predominantly the trans configuration of bridgehead hydrogens. Reduction via catalytic hydrogenation, e.g. using palladium on carbon, gives predominantly the cis configuration of bridgehead hydrogens. If A represents a keto function this may also be reduced together with the bridgehead double bond if a suitable reducing agent is used, e.g. borane dimethylsulphide complex in a polar solvent such as tetrahydrofuran, to give compounds of formula IA where A represents $CH_2$.

Process d) and (G) may be carried out using borohydride reduction of a quaternary salt of the compound of formula XII or tetrahydroquinoline of formula I using appropriate quantities, depending on the degree of reduction, to give compounds of formula IA having a nitrogen ring double bond. Stronger reducing agents or conditions, e.g. borohydride and precious metal catalyst at reflux, gives the fully saturated ring system.

With regard to process (e) and (F) conversions may be carried out by known means, e.g. an alcohol may be formed from an ester substitutent by reduction using lithium borohydride with heating if desired in the presence of an inert solvent, e.g. tetrahydrofuran. Under more vigorous conditions, e.g. reflux, reduction of a keto A group (i.e. A is C=O) may also occur to give a compound of formula IA wherein A is CH$_2$. Bridgehead double bonds may likewise be reduced. Processes (e) and (F) also includes conversion of substituents on R$^4$ and/or R$^3$ when each represents an aromatic radical. Such methods are well known in the art. For example an alkoxy substituent can be converted to hydroxy using boron tribromide. An arylmethoxy substituent can be hydrogenated to give hydroxy. Nitro substituents can be reduced to amino substituents. Amino substituents can be acylated e.g. using an acyl halide to give acylamino, or sulphonylated to give a sulphonamide, or alkylated to give an alkylamino, e.g. by reduction alkylation.

With regard to process (f) the reaction may be conveniently carried out under conditions suitable for the Wolff-Kishner (Organic Reactions IV p 373 (1948) and Merck Index 7th Edn. 1960 p 1479) to give the compound of formula IA wherein Y is CH$_2$.

Processes (g) and (H) may be conveniently carried out using a reducing agent e.g. a trialkylsilane under acidic conditions such as trifluoroacetic acid. As a by-product hydroxy substitution can also occur to give a compound of formula IA wherein R$^8$ is hydroxy.

Process (h) may be carried out by catalytic hydrogenation e.g. using Pd on carbon catalyst under acidic conditions such as glacial acetic acid.

Process (i) may be conveniently carried out using a suitable reducing agent such as borane dimethylsulphide, lithium borohydride or lithium aluminium hydride to reduce the amide ketone.

As mentioned above standard resolution techniques can be used in process (j) to isolate enantiomeric forms of the compounds of formula I and IA. Such techniques are well known in the art.

Where necessary in the reactions described herein protecting groups may be used to protect reactive sites during a reaction and removed thereafter.

Once a compound of formula I is prepared containing a reactive substituent group or site, e.g. an alkanoyloxy substituent, or an acidic proton, then such compounds may be converted to a different compound of formula I, e.g. hydrolysed to give corresponding hydroxy compounds of formula I. Compounds of formula I having an acidic proton may be metallated e.g. lithiated, and reacted with an electrophile e.g. R' Br or R" Br to give other compounds of formula I. Similarly compounds of formula I containing a hydroxy group may be acylated, e.g. using alkanoyl halides to give corresponding alkanoyl compounds of formula I. Similarly when an alkoxy substituent is present then such compounds may be dealkylated using standard procedures to give corresponding hydroxy compounds of formula I. Accordingly compounds of formula I may also be intermediates for other compounds of formula I.

As discussed above starting materials for the processes described herein are known compounds or can be made by analogous methods for known compounds.

Compounds of formula (IX) may be prepared by one of the following:

i) reacting an appropriately substituted 1,3-cyclohexadione with an appropriate aminoacrolein of formula:

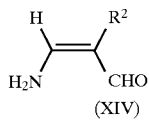

(XIV)

to give a tetrahydroquinoline, quaternising and reducing to give a compound of formula (IX) (according to process (d)) or ii) reacting a compound of formula:

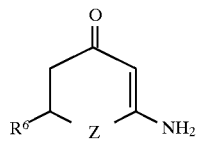

(XV)

with a compound of formula:

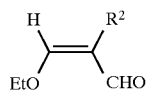

(XVI)

wherein Z, R$^2$ and R$^6$ are as defined above, to give a tetrahydroquinoline compound and reducing as above according to process (d) to give a compound of formula (IX); or iii) reacting a compound of formula (XV) with a compound of formula:

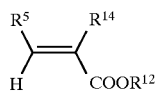

(XVII)

wherein COOR$^{12}$ is an ester group; to give a compound formula (XVIII)

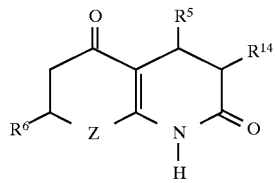

(XVIII)

which is protected and reduced using e.g. LiBH$_4$ or LiAlH$_4$ to give a compound of formula IX.

When R$^{14}$ is hydrogen it can be converted to other values of R$^2$ by reacting a suitably protected (e.g. 1-NH and 5-oxo protected) anionic form with an appropriate electrophile, e.g. ClCOO(C$_1$–C$_6$ alkyl) or ClCH$_2$OCH$_2$CH$_2$SiMe$_3$ which forms are or can be converted to the required R$^2$ group. Protecting groups for the 5-oxo group include ketals or dithiolanes. The protected form may be reduced to give the corresponding piperidine analogue of formula IX i.e. where A is CH$_2$ and R$^4$ is hydrogen. The nitrogen in the 1-position may be protected by —SiMe$_2$$^t$Bu. Different R$^4$ groups can be introduced by alkylation of the 1-sodio salt.

Compounds of formula (X) can be prepared by (i) reacting a ketal protected compound of formula:

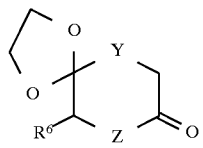

(XIX)

with a compound of formula (XX):

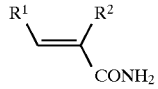

(XX)

where Y, Z, R$^2$, R$^5$ and R$^6$ are as defined above, or R$^2$ is convertible thereto, to give a corresponding compound of formula (X) wherein A is a keto group and the bridgehead double bond is present followed by reduction of the keto group, e.g. using LiBH$_4$ and deprotection to remove the ketal, or (ii) reacting a compound of formula (XIX) with an aminoacrolein of formula:

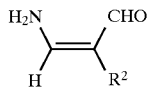

wherein R² is as defined above, and quaternising and reducing the tetrahydroquinoline product according to process (d) and removing the ketal group.

This invention also provides novel intermediates for preparing the active compounds of this invention, and processes for preparing them. In particular this invention provides compound of formula II, III and IV as hereinbefore defined and processes for preparing them.

The compounds of this invention may be obtained in free base form or as acid addition salts as desired. Examples of such salts include salts with pharmaceutically acceptable organic or inorganic acids such as hydrochloric, hydrobromic, hydroiodic, sulphuric, phosphoric, nitric, acetic, citric, tartaric, fumaric, succinic, malonic, formic, maleic acid or organosulphonic acids such as methanesulphonic or p-toluenesulphonic acids.

When acidic substituents are present it is also possible to form salts by treatment with bases, to give for example alkali metals (such as sodium) or ammonium salts. Such salts of the compounds of formula I are included within the scope of this invention.

When basic substituents are present then quaternary ammonium salts may be formed by quaternizing with an alkylating agent such as alkyl or aralkyl halides.

This invention also provides pharmaceutical compositions comprising a compound of formula I or VIII or a pharmaceutically acceptable salt thereof and a pharmaceutically acceptable carrier. For the pharmaceutical compositions any suitable carrier known in the art can be used. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or table disintegrating agents; it can also be encapsulating material. In powders the carrier is a finely divided solid which is in admixture with the the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier, to give a capsule in which the active ingredient (with or without other carrier) is surrounded by carriers, which is thus in association with it. Similarly cachets are included.

Sterile liquid form compositions include sterile solutions, suspensions, emulsions, syrups and elixirs. The active ingredient can be dissolved or suspended in a pharmaceutically acceptable carrier, such a sterile water, sterile organic solvent or a mixture of both.

The active ingredients can often be dissolved in a suitable organic solvent, for instance aqueous propylene glycol containing from 10 to 75% of the glycol by weight is generally suitable. Other compositions can be made by dispersing the finely-divided active ingredient in aqueous starch or sodium carboxymethyl cellulose solution, or in a suitable oil, for instance arachis oil. The composition may be administered orally, nasally, rectally or parenterally.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 1 to 500 mg or more, e.g. 25 mg to 250 mg, according to the particular need and the activity of the active ingredient. The invention also includes the compounds in the absence of carrier where the compounds are in unit dosage form. Based on the results from animal studies the dosage range for the treatment of humans using a compound of formula I will be in the range from about 1 mg to 2 g per day depending on the activity of the compound and the disease to be treated.

For certain of the abovementioned conditions it is clear that the compounds may be used prophylactically as well as for the alleviation of acute symptoms. References herein to "treatment" or the like are to be understood to include such prophylactic treatment, as well as treatment of acute conditions.

The following Examples illustrate the invention and methods for preparing compounds of the invention. In the Examples relative configurations of optical centres are denoted using the R,S notation. As used herein (±)-(3RS, 4aRS,6SR,8aSR) means a racemic mixture of the 3R,4aR, 6S,8aS and 3S,4aS,6R,8aR enantiomers. Where the optical rotation is known but the absolute configuration is not then the following is used: (+)-(3R,4aR,6S,8aS) or (3S,4aS,6R, 8aR) for example.

EXAMPLE 1

1,2,3,4,4a,5,6,7,8,8a-Decahydro-3-hydroxymethyl-6-((4-methoxyphenyl)methyl)quinoline a) 4-((4-Methoxyphenyl)methyl)cyclohexanone (3.87 g) was dissolved in toluene (150 ml) containing morpholine (7.8 ml) and p-toluenesulphonic acid (0.1 g) and the mixture was heated at reflux. Water generated during the reaction was collected using a Dean and Stark trap. After 18 hours the reaction mixture was evaporated under reduced pressure and when all the morpholine had been removed, the residue was redissolved in toluene (100 ml) and cooled to ice temperature. To this solution was added ethyl 2-cyanoacrylate (5 g) with rapid stirring. After 18 hours the reaction mixture was evaporated under reduced pressure and the residue dissolved in 85% aqueous acetic acid. After 30 minutes the reaction mixture was diluted with water and extracted into ethyl acetate. The organic phase was dried (MgSO₄) and evaporated under reduced pressure. The residue was purified by chromatography, first on silica using ethyl acetate as eluent and then on silica using dichloromethane as eluent. The solvent was evaporated under reduced pressure to give 2-cyano-3-[3-(4-methoxyphenyl)methyl-6-oxocyclohexanyl]propanoic acid ethyl ester (51.4 g, 83%).

b) 2-Cyano-3-(3-(4-methoxyphenyl)methyl-6-oxocyclohexanyl)propanoic acid ethyl ester (2.43 g) was added to 15% w/v solution of HBr in acetic acid at 5° C. and stirred for 30 minutes. The reaction mixture was evaporated under reduced pressure and washed with saturated sodium carbonate solution. The mixture was extracted into ethyl acetate and the organic phase dried (MgSO$_4$) and evaporated. The residue was diluted with ether and allowed to crystallise to give ethyl 3,4,5,6,7,8-hexahydro-6-((4-methoxyphenyl)methyl)quinolin-2[1H]-one-3-carboxylate (0.5 g) mp. 143°–145° C.

Analysis: C$_{20}$H$_{25}$NO$_4$ requires C, 69.9; H, 7.3; N, 4.1; Found: C, 69.9; H, 7.55; N, 4.0%.

c) Ethyl 3,4,5,6,7,8-hexahydro-6-((4-methoxyphenyl) methylquinolin-2[1H]-one-3-carboxylate (0.35 g) (prepared according to step a) was dissolved in dichloromethane (1 ml) and triethylsilane (1.5 ml) was added. The solution was cooled with ice. TFA (1.5 ml) was added and the mixture was left to stir 1.5 hours. The reaction mixture was evaporated under reduced pressure and the residue dissolved in chloroform. The chloroform solution was washed with saturated sodium carbonate solution, dried (MgSO$_4$) and evaporated. The residue was suspended in ether, filtered and the solid obtained was recrystallised from ethyl acetate to give ethyl 3,4,4a,5,6,7,8,8a-octahydro-6-((4-methoxyphenyl) methyl)quinolin-2[1H]-one-3-carboxylate (0.14 g) mp 142°–144° C. d) Ethyl 3,4,4a,5,6,7,8,8a-octahydro-6-(4-methoxyphenyl)methylquinolin-2[1H]-one-3-carboxylate (0.47 g) (prepared according to step c) was suspended in ether (5 ml). 2M Lithium borohydride solution in THF (4 ml) and toluene (4 ml) was added and the reaction mixture heated at 100° C. for 2 hours. The reaction mixture was evaporated at reduced pressure and the residue was acidified with 2M HCl (4.5 ml) and further diluted with water (20 ml). The aqueous solution was extracted into chloroform and the organic solution washed with sodium bicarbonate solution, dried (MgSO$_4$) and evaporated. The residue was purified by chromatography on silica using 5–20% v/v methanol in chloroform as eluent. The fractions eluting with 20% methanol were evaporated to give the hydrochloride hemihydrate of the title compound, (80 mg), mp 260°–263° C.

Analysis: C$_{18}$H$_{27}$NO$_2$.HCl.½H$_2$O requires: C, 64.6; H, 8.7; N, 4.2% Found: C, 64.3; H, 8.7; N, 4.3%.

EXAMPLE 2

(±)-(3RS,4aSR,6RS,8aRS)-1,2,3,4,4a,5,6,7,8,8a-Decahydro-3-hydroxymethyl-6-((4-methoxyphenyl)methyl)quinoline a) In a manner analogous to Example 1 step b), but using THF solvent instead of CH$_2$Cl$_2$, ethyl 3,4,4a,5,6,7,8,8a-octahydro-6-((4-methoxyphenyl)methyl)quinolin-2[1H]-one-3-carboxylate was prepared as a 60:40 w/w mixture of (±)-(3RS,4aSR,6RS,8aRS) to (±)-(3SR,4aSR,6RS,8aRS) isomers). This product was suspended in THF (20 ml) at 0° C. and an ice cold solution of 1M lithium borohydride in THF (13.1 ml) was added. The mixture was left to stir 5½ hours at 0° C. and then was added to methanolic hydrogen chloride (120 ml). The acidic solution was left to stand 18 hours and was then evaporated. The residue was dissolved in chloroform and washed with saturated sodium carbonate solution, water and then brine. The organic solution was dried (MgSO4), evaporated and the residual oil was left to stir in hexane containing a small quantity of ethyl acetate for 3 days. The resin obtained was purified by repeated chromatography on a 4 mm "Chromatotron" plate. The later running fractions were combined to give 0.2 g of (±)-(3RS,4aRS,6SR,8aSR)-3,4,4a,5,6,7,8,8a-octahydro-3-hydroxymethyl-6-((4-methoxyphenyl)methyl)quinolin-2[1H]-one.

b) In a manner analogous to Example 1, (±)-(3RS,4aRS,6SR,8aSR)-3,4,4a,5,6,7,8,8a-octahydro-3-hydroxymethyl-6-((4-methoxyphenyl)methyl)quinolin-2[1H]-one (prepared according to step a)) was reduced by heating at 100° C. in the presence of lithium borohydride solution in THF/toluene to give the title compound, mg. 282°–4° C. (HCl, hemihydrate salt).

Analysis: C$_{18}$H$_{27}$NO$_2$.HCl.½ H$_2$O requires: C, 64.6; H, 8.7; N, 4.2 Found: C, 64.7; H, 8.6; N, 4.1%.

EXAMPLE 3

(±)-(3RS,4aRS,6SR,8aSR)-1,2,3,4,4,a,5,6,7,8,8a-Decahydro-3-hydroxymethyl-6-((4-methoxyphenyl)methyl)quinoline In a manner analogous to Example 2 step b), (±)-3,RS, 4aSR,6RS, 8aRS)-3,4,4a,5,6,7,8,8a-octahydro-3-hydroxymethyl-6-((4-methoxyphenyl)methyl)quinolin-2 [1H]-one (isolated from later running fractions from Example 2 step a)) is reduced by heating at 100° C. in the presence of lithium borohydride solution in THF/toluene to give the title compound; mp. 162°–164° C. (HCl, ¼ hydrate).

Analysis: C$_{18}$H$_{27}$NO$_2$.HCl.¼ H$_2$O requires: C, 65.2;H, 8.3; N, 4.4% Found: C, 65.4; H, 8.7; N, 4.2%.

EXAMPLE 4

(±)-(3RS,4aRS,6SR,8aRS)-1,2,3,4,4a,5,6,7,8,8a-Decahydro-3-hydroxymethyl-6-((4-methoxyphenyl)methyl)quinoline a) Paraformaldehyde (200 g) in H$_2$O (300 ml) was heated at reflux and treated with conc. H$_2$SO$_4$(1 ml). The reaction was refluxed for 3 hours, cooled and added to triethylphosphonoacetate (255 g). The mixture was stirred vigorously at room temperature whilst adding a saturated solution of potassium carbonate (280 g). After 18 hours the reaction mixture was treated with saturated NH$_4$Cl solution (375 ml), extracted into diethyl ether, dried (Na$_2$SO$_4$) and concentrated in vacuo. The resulting ethyl 2-hydroxymethylacrylate was distilled at 80° C. under 5 mmHg and used in the following step.

b) 4-(4-Methoxyphenyl)methylcyclohexanone (18 g) in toluene (500 ml) was treated with pyrrolidine (9 g) and a catalytic amount of p-toluenesulphonic acid. The reaction mixture was heated at reflux for 3 hours, with Dean-Stark water separation. The solution was then concentrated in vacuo, toluene was added and the solution concentrated again to remove remaining traces of pyrrolidine. The residual oil was dissolved in absolute ethanol (250 ml) and treated with ethyl 2-hydroxymethylacrylate (12.6 g) from step a). The reaction mixture was stirred at room temperature for 48 hours and brought to pH 5–6 with 20% aqueous acetic acid. After stirring for ½ hour the mixture was concentrated in vacuo and partitioned between water and ethyl acetate. The organic layer was dried (Na$_2$SO$_4$) and chromatographed on SiO$_2$ using diisopropyl ether as solvent to give 3,4,4a,5,6,7,8,8a-octahydro-3-ethoxycarbonyl-8a-hydroxy-6-(4-methoxyphenyl)methyl-2H-benzo-[b]pyran (21 g).

c) 3,4,4a,5,6,7,8,8a-Octahydro-3-ethoxycarbonyl-8a-hydroxy-6-(4-methoxyphenyl)methyl)-2H benzo[b]pyran (21 g) in methanol (100 ml) was heated under reflux with ammonium acetate (40 g) for 18 hours. The mixture was evaporated to dryness and the residue partitioned between water and chloroform. The chloroform extract was dried (Na$_2$SO$_4$), treated with charcoal and evaporated to give an oil. This was crystallised from ethylacetate to give 3,4,5,6, 7,8-hexahydro-3-hydroxymethyl-6-((4-methoxyphenyl) methyl)quinolin-2[1H]-one, mp 165°–168° C.

d) 3,4,5,6,7,8-Hexahydro-3-hydroxymethyl-6-((4-methoxyphenyl)methyl)quinolin-2[1H]-one (24.7 g) (prepared according to step c) in THF (200 ml) was treated with borane-dimethylsulphide complex (25 ml) and stirred at room temperature under argon for 18 hours. The reaction mixture was then treated with aqueous acetic acid (20%) until pH 5 and then stirred for an hour. HCl was added until the mixture was strongly acidic and then the solvent removed in vacuo. The residue was dissolved in methanol, concentrated to remove borate esters then converted to the hydrochloride salt (28 g). This salt was recrystallised from ethyl acetate-methanol (200 ml–15 ml) to yield a fraction (15.7 g) containing 34% of the title compound. This fraction was triturated with ethyl acetate, converted to the free base and fractionally crystallised from t-butylmethyl ether, yielding a fraction containing 84% of the title compound. Further recrystallisation was carried out from t-butylmethyl ether diethylether (1:1) and the product converted to the hydrochloride salt (1.8 g), mp 288°–289.5° C.

Analysis: $C_{18}H_{27}NO_2.HCl$ requires C, 66.4;H, 8.6;N, 4.3 Found: C, 66.6; H, 8.7; N, 4.3%

EXAMPLE 5

(−)-(3S,4aR,6S,8aS)-1,2,3,4,4a,5,6,7,8,8a-Decahydro-3-hydroxymethyl-6-((4-methoxyphenyl)methyl)quinoline 3,4,5,6,7,8-Hexahydro-3-hydroxymethyl-6-((4-methoxyphenyl)methyl)quinolin-2[1H]-one(8.5 g) (prepared according to Example 4 steps a–c) in THF (50 ml) was treated with borane-dimethylsulphide (43 ml, 2M in THF) and stirred at room temperature for 18 hours under argon. Aqueous acetic acid (20 ml) was added and the mixture stirred for 1 hour. Ethereal HCl (5 ml) was added and the mixture refluxed for 1 hour. Evaporation of the solvent in vacuo gave a residue which was dissolved in methanol and evaporated to give an oil. This was crystallised from t-butylmethyl ether. The product was dissolved in $CH_2Cl_2$, washed with water and the organic phase dried, $(Na_2SO_4)$, concentrated in vacuo to give a residue (1.4 g). This was dissolved in ethyl acetate (50 ml) and treated with di-p-toluoyl-D-tartaric acid (2.56 g) in ethyl acetate (20 ml). A precipitate formed and was taken back into solution by addition of a further 30 ml of ethyl acetate and methanol (6 ml) and warming. On cooling crystals were obtained (0.7 g) showing a 85:15 mixture diastereomeric salts. The mixture was converted to the di-p-toluoyl-L-tartaric acid salts and recrystallised from acetonitrile. The title compound was obtained as the di-p-toluoyl-L-tartaric acid salt and converted to its hydrochloride salt, mp 310°–312° C., $[\alpha]_D^{25}$= −27° (1% MeOH).

Analysis: $C_{18}H_{27}NO_2$. HCl requires: C, 66.4; H, 8.6; N, 4.3 Found: C, 66.1; H, 9.0; N, 4.1%.

EXAMPLE 6

(+)-(3R,4aS,6R,8aR)-1,2,3,4,4a,5,6,7,8,8a-Decahydro-3-hydroxymethyl-6-((4-methoxyphenyl)methyl)quinoline (±)-(3RS,4aSR,6RS,8aRS)-1,2,3,4,4a,5,6,7,8,8a-Decahydro-3-hydroxymethyl-6-((4-methoxyphenyl)methyl)quinoline (6.7 g) (prepared according to Example 2) in ethyl acetate (140 ml) was treated with (+)-di-p-toluoyltartaric acid (10.5 g) in ethyl acetate (70 ml). The resulting salt mixture was recrystallised until a ration of isomers of ca. 35:65 as achieved. The salt mixture was then converted to the free base and treated with (−)-di-p-toluoyl tartaric acid. Fractional recrystallisation using methyl acetate or acetonitrile as solvent was carried out until a 10:90 isomer mixture was obtained. The salt mixture was then converted to the free base and treated with (−)-1,1'-bi-naphthyl-2,2'-diylhydrogen phosphate and a solid crystallised. The product was recrystallised from acetone and converted back to the free base and treated with HCl to give substantially pure title (+)-enantiomer as the hydrochloride salt, mp 303°–5° C., $[\alpha]_D^{27}$=+10° (1% $CHCl_3$).

Analysis: $C_{18}H_{27}NO_2.HCl.1/2\ H_2O$ requires: C, 64.6; H, 8.7; N, 4.2 Found: C, 64.9; H, 8.4; N, 3.0%

EXAMPLE 7

(+)-(1'R,4aS,6R,8aR)-1,2,3,4,4a,5,6,7,8,8a-Decahydro-6-(4-methoxyphenyl)methyl)-1-(1'-phenylethyl)quinoline A. 4-Methoxybenzylcyclohexanone (43.68 g, 0.2 mol) was dissolved in toluene (250 ml). To this solution pyrrolidine (25 ml, 0.3 mol) was added together with a catalytic amount of p-toluenesulphonic acid. The reaction mixture was refluxed with a Dean and Stark apparatus for 20 hours. Once the predicted amount of water had been collected, the solvent was removed under vacuum. Excess pyrrolidine was removed by adding a little toluene and evaporating under reduced pressure.

The resulting liquid was dissolved in methanol (200 ml) and to the resulting stirred solution methyl acrylate (18 ml, 0.2 mol) dissolved in methanol (50 ml) was added dropwise. This was stirred for 20 hours at room temperature.

The resulting liquid was neutralised with sodium bicarbonate and the product extracted into dichloromethane. The solution was then passed through a bed of Florisil. The solvent was evaporated leaving an oil. This material was purified by distillation. 2-( 2-Methoxycarbonylethyl)-4-(4-methoxybenzyl)cyclohexanone distilled at 155° C., 0.05 mmHg (30.43 g).

B. The ketone prepared in step (A) above (34 g, 112 mmol) was heated at reflux with R(+)-α-methylbenzylamine (14.8 g 122 mmol) and toluene (500 ml) in the presence of a catalytic amount of p-toluenesulphonic acid using a Dean and Stark water separator. After 24 hours the reaction mixture was concentrated in vacuo, dissolved in absolute ethanol and hydrogenated over Raney nickel under 50 psi hydrogen at room temperature. After 4 days the catalyst was filtered off and the filtrate concentrated in vacuo. The isomer mixture was separated by chromatography on a silica column using diisopropylether as eluent to give methyl (1'R, 1S,2R,5R)-5-((4-methoxyphenyl)-2-(1'-phenylethylamino) ethylamino)cyclohexanepropionate (Rf 0.35).

C. The product of step (B) (10 g) was heated in toluene (200 ml) in the presence of acetic acid (2 ml) for 24 hours. After cooling the acetic acid was removed by washing with a saturated aqueous sodium bicarbonate solution. The organic phase was separated, dried $(Na_2SO_4)$ and evaporated. The residue was chromatographed on a silica column using diisopropyl ether as eluent to give (+)-(1'R,4aS,6R, 8aR)-3,4,4a,5,6,7,8,8a-octahydro-6-((4-methoxyphenyl) methyl)-1-(1'-phenylethyl)quinolin-2[1H]-one, mp 103°–4° C.

D. (+)-(1'R,4aS,6R,8aR)-3,4,4a,5,6,7,8,8a-Octahydro-6-(4-methoxyphenyl)methyl)-1-(1'-phenylethyl)quinolin-2 [1H]one (1.9 g, 5 mmol) in tetrahydrofuran (20 ml) was treated at room temperature with $BH_3.DMS$ (1.6 ml, 15 mmol) and stirred under argon for 18 hours. The reaction was quenched with water, stirred for 5 minutes then acidified with 2M HCl. After stirring for a further 30 minutes the organic solvent was evaporated in vacuo and the residue treated with methanol and evaporated down again. The remaining aqueous residue was basified with ammonia and extracted into diethyl ether. The organic phase was dried (NaSO$_4$) and evaporated in vacuo, to yield 1.35 g of the title compound. The resulting solid was chromatographed on a silica column using diisopropyl ether as eluent. The relevant fractions were combined and evaporated down yielding 0.8 g of the title compound, mp 143°–4° C., $[\alpha]^{25}_D$=+28° (1% CHCl$_3$).

Analysis: C$_{25}$H$_{33}$NO requires: C, 82.6; H, 9.2; N, 3.9 Found: C, 82.7; H, 9.5; N, 3.9%.

EXAMPLE 8

(+)-(1'R,4aS,6S,8aR)-1,2,3,4,4a,5,6,7,8,8a-Decahydro-6-((4-methoxyphenyl)methyl)-1-(1'-phenylethyl)quinoline A. Also isolated from the chromatography step of Example 7B) was methyl (1'R,1S,2R,5S)-5-((4-methoxyphenyl)methyl-2-(1'-phenylethylamino)cyclohexanepropionate having an Rf value of 0.71.

B. The product of Step (A) (14 g 342 mmol) was heated under reflux in toluene (200 ml) in the presence of acetic acid (3 ml). After 24 hours further acetic acid was added (1 ml) and the mixture refluxed a further 4 hours. The reaction mixture was concentrated in vacuo and filtered through a pad of silica using diisopropylether as eluent. The filtrate was evaporated to give the title compound as an oil (12.2 g). This was crystallised from diisopropyl ether to give (−)-(1'R,4aS,6S,8aR)-3,4,4a,5,6,7,8,8a-octahydro-6-((4-methoxyphenyl)methyl)-1-(1'-phenylethyl)quinolin-2[1H]-one, mp 68°–9° C., $[\alpha]^{24}_D$=−27° (1% CHCl$_3$).

C. (−)-(1'R,4aS,6S,8aR)-3,4,4a,5,6,7,8,8a-Octahydro-6-((4-methoxyphenyl)methyl)-1-(1'-phenylethyl)quinolin-2[1H]one (2 g, 5.3 mmol) in tetrahydrofuran (20 ml) was treated at room temperature with BH$_3$.DMS (1.6 ml, 15 mmol) in a manner analogous to Example 7 to give the title compound. This was purified by chromatography using a silica column and diethyl ether as eluent, $[\alpha]^{26}_D$=+9° (1% CHCl$_3$).

Analysis: C$_{25}$H$_{33}$NO requires: C, 82.6; H, 9.1; N, 3.9% Found: C, 82.8; H, 9.4; N, 3.8%.

EXAMPLE 9

(−)-(4aS,6S,8aR)-3,4,4a,5,6,7,8,8a-Decahydro-6-((4-methoxyphenyl)methyl)quinoline (a) 2-(Methoxycarbonylethyl)-4-(4-methoxybenzyl)cyclohexanone (118 g, 0.399 mol) was dissolved in toluene (1 l) with R (+)-α-methylbenzylamine (52 g, 0.43 mol) and p-toluenesulphonic acid (0.2 g). The reaction mixture was heated under reflux in a Dean Stark apparatus for 24 hours. The solvent was removed under vacuum and the residue was hydrogenated in ethanol (800 ml) over Raney nickel at room temperature under 50 psi for four days. The catalyst was filtered off and the solvent of the filtrate was then evaporated under vacuum. The resulting oil was then chromatographed on a silica gel with a diisopropyl ether and hexane solvent system (ratio 1:1). The first fraction yielded methyl (1'R,1S,2R,5S)-5-((4-methoxyphenyl)methyl)-2-(1'-phenylethylamino)cyclohexanepropionate (50.5 g).

(b) The product of step (a) (18.78 g, 0.046 mol) was dissolved in methanol (200 ml) and added to a slurry of isopropanol and palladium on carbon. The solution was then shaken in a Parr apparatus at 50° C. and at 50 psi under hydrogen for four days. The solution was filtered and the filtrate was then evaporated to give a cream solid. This was then treated with saturated sodium hydrogen carbonate and stirred for 2 hours. The solid was then filtered off and recrystallised from methanol to give (−)-(4aS,6S,8 aR)-3,4,4a,5,6,7,8,8a-octahydro-6-((4-methoxyphenyl)methyl)quinolin-2(1H)-one, mp 199°–200° C. (7.38 g).

(c) (−)-(4aS,6S,8aR)-3,4,4a,5,6,7,8,8a-Octahydro-6-((4-methoxyphenyl)methyl))quinolin-2(1H)-one (0.691 g, 0.0025 mol) was dissolved in dry THF and stirred under argon. Borane-dimethyl sulphide complex (0.6 ml, 0.007 mol) was added dropwise and the mixture was stirred for 18 hours. The reaction was quenched with water and the solvent evaporated to give a white solid which was dissolved in methanol. 2N HCl (10 ml) was added and the solution was refluxed for four hours. The solution was cooled and neutralised with ammonia. The methanol was removed under vacuum and the product was extracted into diethyl ether. The extract was then dried over sodium sulphate, and filtered and the solvent evaporated to leave a yellow oil. The oil was dissolved in diethyl ether, diluted with hexane and a few drops of the ethereal HCl added to precipitate out the hydrochloride salt of the title compound which was filtered and dried, $[\alpha]^{26}_D$=−39° (c=1 MeOH), mp 238°–240° C.

Analysis: C$_{17}$H$_{25}$NO.HCl.0.25H$_2$O requires; C, 68.0; H, 8.9; N, 4.7 Found: C, 68.3; H, 9.0; N, 4.5%.

EXAMPLE 10

(−)-(1'R,3R,4aR,6S,8aR)-1,2,3,4,4a,5,6,7,8,8a-Decahydro-3-hydroxymethyl-6-((4-methoxyphenyl)methyl)-1'-phenylethyl)quinoline (a) (−)-(1'R,4aS,6S,8aR)-3,4,4a,5,6,7,8,8a-Octahydro-6-((4-methoxyphenyl)methyl)-1-(1'-phenylethyl)quinolin-2[1H]-one (2 g, 5.3 mmol) prepared according to Example 8B in THF (5 ml) was added to lithium tetramethylpiperidide in THF (20 ml) under argon at −50° C. The reaction was allowed to warm to room temperature and was stirred for 2 hours. The resulting anion was treated with trimethylsilylethoxymethyl chloride (1 g, 6.0 mmol) at 0° C. then stirred at room temperature for 1 hour. Solvent was removed in vacuo and the residue partitioned between ethyl acetate and 2M HCl. The organic phase was separated, dried (Na$_2$SO$_4$) and concentrated to yield an oil. The oil was chromatographed on a silica column using diisopropyl ether as eluent and the major isomer was collected (0.8 g, 1.6 mmol). This was dissolved in dichloromethane (6 ml) and treated with BF$_3$.Et$_2$O (2 ml, 1.6 mmol) at room temperature and stirred for 10 minutes. The reaction mixture was diluted with dichloromethane (50 ml) washed with NaCO$_3$ solution, (15 ml), and the organic phase was separated, dried (Na$_2$SO$_4$) and concentrated to yield 0.7 g of an oil. Minor impurities were removed by chromatography on a silica column using ethyl acetate as eluent to give (−)-(1'R,3S,4aR,6S,8aR)-3,4,4a,5,6,7,8,8a-Octahydro-3-hydroxymethyl-6-((4-methoxyphenyl)methyl)-1-(1'-phenylethyl)quinolin-2[1H]-one as an oil, $[\alpha]^{27}_D$=−7° (1% CHCl$_3$).

(b) (−)-(1'R,3S,4aR,6S,8aR)-3,4,4a,5,6,7,8,8a-Octahydro-3-hydroxymethyl-6-((4-methoxyphenyl)methyl)-1-(1'-phenylethyl)quinolin-1[1H]-one (0.86 g 2.1 mml) (prepared according to step (a)) in THF (10 ml) was treated at room temperature with BH$_3$.DMS (0.63 ml, 6.3 mol) and stirred under argon for 18 hours. The reaction was quenched with water, stirred for five minutes then acidified with 2M HCl. After stirring for 80 minutes the organic solvent was evaporated in vacuo and the remaining aqueous phase treated with methanol and evaporated down again. The residue was basified with aqueous ammonia and extracted into diethyl ether. The organic phase was separated, dried (Na$_2$SO$_4$) and concentrated in vacuo. The residual oil was chromatographed (20% EtOAc:hexane:SiO$_2$) and converted to the hydrochloride sesquihydrate salt, $[\alpha]^{27}_D$=−8°, (1%, MeOH), mp 138°–140° C.

EXAMPLE 11

(−)-(1'S,3R,4aR,6S,8aS)-1,2,3,4,4a,5,6,7,8,8a-Decahydro-3-hydroxymethyl-6-((4-methoxyphenyl)methyl)-(1'-phenylethyl)quinoline A)(i) (−)-(1'S,4aS,6E,8aS)-1,3,4,4a,5,7,8,8a-Octahydro-6-((4-methoxyphenyl)methylidene)-1-(1'-phenylethyl)quinolin-2-one was prepared by heating 1,4-cyclohexanedione monoethylene ketal (100 g 0.64 mol), pyrrolidine (80 ml, 0.96 mol) and p-toluenesulphonic acid (0.3 g) under reflux in toluene (600 ml) with Dean-Stark water separation. After 3 hours the reaction was evaporated down under reduced pressure and the residue re-dissolved in toluene and concentrated again to give an oil. This oil was dissolved in methanol (500 ml) and treated with methyl acrylate (60 ml, 0.67 mol). The reaction was stirred at room temperature under Ar overnight. After 18 hours the reaction was evaporated in vacuo and the residual oil distilled under reduced pressure. The product, S-(−)-α-methylbenzylamine (50 g, 0.41 mol) and p-toluenesulphonic acid (0.3 g) were heated under reflux with Dean-Stark water separation in toluene (500 ml) for 24 hours. The toluene was evaporated off and the residual oil redissolved in methanol (250 ml), cooled to 0° C. and treated with sodium borohydride (15.2 g, 0.4 mol), portion wise. The reaction was stirred for 1 hour at room temperature, then quenched with water (250 ml). After stirring for 30 minutes the methanol was removed in vacuo and the residue partitioned between aqueous ammonia and diethyl ether. The organic phase was separated, dried ($Na_2SO_4$) and evaporated to give an oil. The desired isomer, (−)-1'S,3S,4S)-spiro(1,3-dioxalane-2,5')-4'-(1"-phenylethylamino)cyclohex-3'-ane, propanoic acid, methyl ester was isolated by chromatography on $SiO_2$-diisopropylether.

(ii) The isomer from step (i) (ca. 40 g) was heated under reflux in toluene (1.51) with glacial acetic acid (6 ml, 0.1 mol) for 5 hours. The solution was cooled, washed with saturated aqueous sodium bicarbonate solution, dried ($Na_2SO_4$) and concentrated in vacuo. The spiro ketal product was chromatographed on $SiO_2$-ethyl acetate and then heated under reflux in 20% aqueous acetic acid, (300 ml) for 4 hours. The reaction was diluted with water, extracted into diethyl ether, the organic phase washed with saturated sodium bicarbonate solution, dried ($Na_2SO_4$) and evaporated in vacuo. The resulting product was recrystallised from diisopropyl ether yielding (1'S,4aS,8aS)-3,4,4a,5,6,7,8,8a-octahydro-(1'-phenylethyl)-1H-2,6-dioxoquinoline (iii) 4-Methoxybenzyltriphenylphosphonium bromide (44 g, 95 mmol) in toluene (1.251) was refluxed for 18 hours and water collected by Dean-Stark apparatus. Half of the toluene was distilled off and the suspension allowed to cool at room temperature. Tetrahydrofuran (THF) (600 ml) was added and the mixture cooled to −15° C. then treated with nBuLi (59 ml, 95 mmol) under argon. The solution was allowed to warm to 0° C. and was stirred for 2 hours.

(iv) The product of step (ii) previously dried by azeotroping with toluene, (25 g 92 mmol) in THF (200 ml) was added slowly to the anion produced in step (iii) keeping the temperature below 5° C. After stirring for 5 days the triphenylphosphine oxide formed was filtered off and washed with ethyl acetate. The filtrates were evaporated down yielding an oil, which crystallised from ethyl acetate. The mother liquors were filtered through a short pad of $SiO_2$ in ethyl acetate, and the filtrate chromatographed on $SiO_2$ in ethyl acetate-di-isopropyl ether to give two fractions one of which was the desired (−)-(1'S,4aS,6E,8aS)-1,3,4,4a,5,7,8,8a-Octahydro-6-((4-methoxyphenyl)methylidene)-1-(1'-phenylethyl)quinolin-2-one.

B) (1'S,4aS,6E,8aS)-1,3,4,4a,5,7,8,8a-Octahydro-6-((4-methoxyphenyl)methylidene)-1-(1'-phenylethyl)quinolin-2-one was reduced by transfer hydrogenation over palladium black (1 g) in cyclohexene (200 ml) at reflux for 18 hours. The catalyst was filtered off and the filtrate concentrated in vacuo. The resulting oil was crystallised from diisopropyl ether and then recrystallised from the same solvent to give (+)-(1'S,4aS,6S,8aS)-3,4,4a,5,6,7,8,8a-octahydro-6-((4-methoxyphenyl)methyl-1-(1'-phenylethyl)quinoline-2[1H]-one, mp=130°−2° C.

C) (+)-(1'S,4aS,6S,8aS)-3,4,4a,5,6,7,8,8a-Octahydro-6-((4-methoxyphenyl)methyl-1-(1'-phenylethyl)quinoline-2[1H]-one (6.38 g 17 mmol) in THF (50 ml) was added to the LiTMP (nBuLi 11.7 ml, TMP 3.14 ml, 18.6 mmol) in THF (40 ml) under argon at −70° C. The reaction was allowed to warm to room temperature and stirred for 1½ hours. The resulting anion was cooled to −78° C. and treated with trimethylsilylethoxymethyl chloride (3.62 ml. 20.5 mmol). The reaction was allowed to warm to room temperature, stirred for 1 hour, concentrated in vacuo and the residue partitioned between 2M HCl and EtOAc. The organic phase was separated, dried ($Na_2SO_4$) and evaporated down. The residue obtained was separated from the starting material by chromatography and the product treated dropwise at 0° C. with $BF_3.OEt_2$ (16 ml, 130 mmol) and stirred for 15 minutes. The reaction was neutralised with saturated $NaHCO_3$ solution and the organic phase separated, dried ($Na_2SO_4$) and concentrated in vacuo. The resulting two isomers were separated by column chromatography ($SiO_2$-EtOAc/hexane (1:1) yielding two fractions. The second fraction eluted was isolated, evaporated and the residue crystallised. This fraction (670 mg) was then added to THF (5 ml) and treated at room temperature under argon with 10M $BH_3.DMS$ (5.0 ml, 5 mmol). The reaction mixture was stirred overnight then quenched with acetic acid, diluted with water and extracted in diethyl ether. The organic layer was back extracted with 2M HCl and the combined aqueous layers basified with aqueous ammonia, then extracted with chloroform. The organic phase was dried ($Na_2SO_4$) and concentrated in vacuo yielding 0.616 g. This product was dissolved in ethyl acetate, charcoal was added and the mixture filtered through a short pad of $SiO_2$ to remove sulphurous contaminants. After conversion to the hydrochloride salt in diethyl ether the title compound was recrystallised from ethyl acetate, mp 121°−2° $[α]^{27}_D$=−13° (1% MeOH)

Analysis: $C_2H_{35}NO_2.HCl.H_2O$ requires: C, 69.7; H, 8.6; N, 3.1 Found: C, 69.5; H, 8.9; N, 3.1%.

EXAMPLE 12

(+)-(3S,4aS,6R,8aR)-1,2,3,4,4a,5,6,7,8,8a-Decahydro-3-hydroxymethyl-6-((4-methoxyphenyl)methyl)quinoline (+)-1'R,3S,4aS,6R,8aR)-1,2,3,4,4a,5,6,7,8,8a-Decahydro-3-hydroxymethyl-6-((4-methoxyphenyl)methyl)-(1'-phenethyl)quinoline, hydrochloride (1.63 g 4.1 mmol, prepared according to Example 19) was hydrogenolysed in 1:1 hexane:ethanol (100 ml) and glacial acetic acid (5 ml) over palladium hydroxide on carbon (200 mg) under 50 psi hydrogen at room temperature. After 24 hours the catalyst was filtered off and the filtrate concentrated in vacuo. The residue was partitioned between water and diethyl ether, the aqueous phase was basified with ammonia, extracted into dichloromethane, dried ($Na_2SO_4$) and concentrated. The residue was converted to the hydrochloride in ethereal HCl, yielding 1.3 g of the title compound as the hydrochloride, quarterhydrate, mp 160°−162° C. $[α]^{24}_D$=+24° (1% $CHCl_3$) on free base Analysis: $C_{26}H_{35}NO_2.HCl.0.25\ H_2O$ requires: C, 68.3; H, 8.6; N, 3.2 Found: C, 68.7; H, 8.5; N, 3.0%.

Analysis: $C_{18}H_{27}NO_2 \cdot HCl \cdot 0.25\ H_2O$ requires: C, 65.4; H, 8.7; N, 4.2% Found: C, 65.6; H, 8.9; N, 4.1%.

EXAMPLE 13

(−)-(1'R,3R,4aR,6S,8aR)-1,2,3,4,4a,5,6,7,8,8a-Decahydro-6-((4-methoxyphenyl)methyl)-3-methyl-1-(1'-phenylethyl)quinoline (A) (−)-(1'R,4aS,6S,8aR)-3,4,4a,5,6,7,8,8a-Octahydro-6-((4-methoxyphenyl)methyl)-1-(1'-phenylethyl)quinolin-2[1H]-one (3 g, 8 mmol) (prepared by reacting methyl (1'R,1S,2R,5S)-5-((4-methoxyphenyl)methyl-2-(1'-phenylethylamino)cyclohexanepropionate with acetic acid) in THF (7.5 ml) was added to LiTMP (nBuLi) 5.4 ml, TMP 1.2 g, 8 mmol) in THF (30 ml) under argon at −70° C. The reaction was allowed to warm to room temperature and stirred for 2 hours. The resulting anion was treated with methyl iodide (1.36 g, 0.6 ml, 9.6 mmol) in THF (2 ml) at −70° C., allowed to warm to room temperature and stirred for 1 hour. The reaction mixture was evaporated down and the residue partitioned between ethyl acetate and 2M HCl. The organic phase was separated, dried ($Na_2SO_4$) and concentrated in vacuo. The resulting oil was chromatographed silica-diisopropylether) and crystallised from hexane to give (−)-(1'R, 3R,4aR,6S,8aR)-3,4,4a,5,6,7,8,8a-octahydro-6-(4-methoxyphenyl)methyl)-3methyl-1-(1'-phenylethyl)quinolin-2[1]-one, (1.5 g), mp 108°–110° C.

(B) The product of step A) (1 g 2.8. mmol) in THF (10 ml) was treated with $BH_3 \cdot DMS$ (0.77 ml, 7.7 mmol) and stirred at room temperature under argon for 18 hours. The reaction was quenched with water, stirred for 5 minutes then acidified with 2M HCl. After stirring for 30 minutes the organic solvent was removed in vacuo. The remaining aqueous phase was treated with methanol and evaporated. The residue was basified with ammonia and extracted in dichloromethane, the organic phase was dried ($Na_2SO_4$) and concentrated in vacuo yielding an oil. The oil was chromatographed ($SiO_2$-EtOAc) and converted to the hydrochloride in ethereal HCl, mp 179°–181° C. $[\alpha]^{25}_D = -7°$ (1% MeOH).

Analysis: $C_{26}H_{35}NO \cdot HCl \cdot 1/2\ H_2O$ requires: C, 73.8; H, 8.8; N, 3.3 Found: C, 73.9; H, 8.9; N, 3.3%.

EXAMPLE 14

(−)-(1'S,4aS,6R,8aS)-1,2,3,4,4a,5,6,7,8,8a-Decahydro-6-(4-methoxyphenyl)methyl)-1-(1'-phenylethyl)quinoline A. Methyl Spiro (1,3-dioxolane-2,3')cyclohexa-6-[1H]one propionate.

1,4-Cyclohexanedione monoethylene ketal (100 g), pyrrolidine (80 ml) and p-toluene sulphonic acid (0.5 g) in toluene (500 ml) were refluxed for 18 hours and the water collected by means of a Dean and Stark apparatus. The toluene was removed under reduced pressure and the residue dissolved in methanol (500 ml), then treated dropwise with methyl acrylate (50 ml). The mixture was stirred at room temperature for 15 hours and a solution of 10% acetic acid was added to bring the mixture to a pH of about 5. Stirring was continued for a further 3 hours and the solvent was removed under reduced pressure. The residue was extracted with chloroform. The combined chloroform extracts were washed with sodium bicarbonate solution, water then dried ($MgSO_4$) and evaporated to give an oil. This was distilled at 128°–132° C. under a pressure of 0.05 mm of Hg to give (89.4 g) of the required title product of step (A).

B. Methyl (1"S,1'R,2'S)spiro(1,3-dioxalone-2,3')-6-(1"-phenylethylamino)cyclohexanepropionate.

The product of step A, (21.26 g 0.087 m) and (S)-(−)-α-methylbenzylamine (10.51 g 0.087 m) in toluene (250 ml) were refluxed for 18 hours and water was collected by means of a Dean and Stark apparatus. The solvent was evaporated and the residue dissolved in ethanol (100 ml) and Raney nickel (ca. 10 g) was added. The mixture was hydrogenated at 50 psi for 3 days. The catalyst was removed by filtration and the solvent removed under reduced pressure. The resulting residue was purified by chromatography on silica using methyl acetate as eluent to give methyl (1"S,1'R,2'S)spiro (1,3-dioxalone-2,3')-6-(1'-phenylethylamino) cyclohexanepropionate (23.76 g).

C. (1"S,4a'R,8a'S)-3',4',4a',5',6',7',8',8a'-Octahydrospiro(1, 3-dioxolane-2,6')-1'-(1"-phenylethyl)quinolin-2'[1H]-one The product of step B (22.7 g, 0.65 m) was refluxed for 4 hours in toluene (50 ml) and glacial acetic acid (3.92 g 0.065 m). The solution was cooled, then washed consecutively with sodium bicarbonate solution, 1N hydrochloric acid and water, then dried ($MgSO_4$) and evaporated to give (1"S,4'aR,8'aS)-3',4',4a',5',6',7',8',8a-octahydrospiro(1,3-dioxolane-2,6')-1'-(1"-phenylethyl)quinolin-2"[1H]-one, (18.78 g).

D. (1'S,4aR,8aS)-3,4,4a,5,6,7,8,8a-Octahydro-1-(1'phenylethyl)quinolin-2,6-dione.

The product of step C (18.7 g, 0.059 m) with pyridinium p-toluene sulphonate (1.75 g) in acetone (90 ml) and water (10 ml) was refluxed for 60 hours. The solvent was removed under reduced pressure and the residue dissolved in ethyl acetate. The organic phase was washed with water, sodium bicarbonate solution, dried ($MgSO_4$) and evaporated. The residue was dissolved in acetone (180 ml) and water (20 ml) with pyridinium p-toluene sulphone (1.75 g) and refluxed for 24 hours and the purification stage above repeated to give (1'S,4aR,8aS)-3,4,4a,5,6,7,8,8a-octahydro-1-(1'-phenylethyl)quinolin-2,6-dione (14.62 g) as a gum.

E. (1'S,4aR,8aS)-3,4,4a,5,6,7,8,8a-Octahydro-6-((4'-methoxyphenyl)methylidine)-1-(1'-phenylethyl)quinolin-2[1H]-one.

4-Methoxybenzyl triphenylphosphonium chloride (10.4 g, 0.25 m) in THF (250 ml) was cooled to −15° C. and treated with n-butyl lithium (1.6M solution in n-hexane, 15.5 ml) and allowed to warm to room temperature and stirred for 18 hours. The anion was cooled to −30° C. and the product of step D (6.72 g 0.025 m) in THF (30 ml) was added and the mixture allowed to warm to room temperature. Water was added followed by ethyl acetate. The organic phase was separated, dried ($MgSO_4$) and evaporated. The mixture was triturated with diisopropyl ether and the solid removed by filtration and discarded. The resulting solution was evaporated to give a gum which was purified by chromatography on silica using ethyl acetate as eluent to give (1'S,4aR,8aS)-3,4,4a,5,6,7,8a-octahydro-6-((4'-methoxyphenyl)methylidene)-1-(1'-phenylethyl)quinolin-2 [1H]-one as a 1:1 mixture of E- and Z-isomers (5.25 g).

F). (+)-(1'S,4aR,6R,8aS)-3,4,4a,5,6,7,8,8a-Octahydro-6-(4-methoxyphenyl)methyl)-1-(1'-phenylethyl)quinolin-2 [1H]-one The benzylidene prepared according to step E (8.3 g) with palladium black (1.0 g) in cyclohexane (100 ml) was refluxed for 24 hours and the catalyst removed by filtration. The solvent was removed under reduced pressure to give a gum. This was purified on silica using diethyl ester as eluent to give the title compound (5.0 g) as a gum.

G) (−)-(1'S,4aS,6R,8aS)-1,2,3,4,4a,5,6,7,8,8a-Decahydro-6-((4-methoxy phenyl)methyl)-1-(1'-phenylethyl)quinoline.

(+)-(1'S,4aR,6R,8aS)-3,4,4a,5,6,7,8,8a-Octahydro-6-((4-methoxyphenyl)methyl)-1-(1'-phenylethyl)quinolin-2[1H]-one (5 g) in THF (100 ml) was treated with borane dimethyl suphide complex (4.2 ml) at room temperature and stirred under argon for 18 hours. Water was added cautiously, followed by 2M HCl and the mixture stirred for 1 hour. The solvent was evaporated and the residue treated with methanol and then evaporated to dryness. Water was added followed by conc. $NH_3$ and the product extracted into diethyl ether. The organic phase was dried (MgSO4) and evaporated to give a gum which was purified on silica eluted with n-hexane:ethyl acetate (4:1). The product was dissolved in diethyl ether and treated with ethereal HCl to give the title compound as the hydrochloride salt, (0.79 g) mp 172°–4° C. $[\alpha]^{26}_D$=–17° (1% in MeOH).

Analysis: $C_{25}H_{33}NO.HCl$ 1/4 $H_2O$ requires: C, 74.2; H, 8.6; N, 3.4 Found: C, 74.4; H, 8.6; N, 3.4%.

EXAMPLE 15

(+)(4aR,6R,8aS)-1,2,3,4,4a,5,6,7,8,8a-Decahydro-6-((4-methoxyphenyl)methyl)quinoline (–)-(1'S,4aS,6R,8aS)-1,2,3,4,4a,5,6,7,8,8a-Decahydro-6-((4-methoxyphenyl)methyl-1-(1'-phenylethyl)quinoline (1.32 g, prepared according to Example 14) in n-hexane:MeOH (1:1, 80 ml) with 10% Pd/C (0.2 g) and glacial acetic acid (5 ml) was hydrogenated at 50 psi for 15 hours. The solution was filtered, evaporated under reduced pressure and the residue treated with sodium carbonate solution to give a product which was extracted into ethyl acetate. The ethyl acetate extract was dried ($MgSO_4$) and evaporated to give a gum. This was dissolved in diethyl ether and treated with ethereal HCl. The resulting precipitate was collected by filtration and dried giving the title compound as the hydrochloride salt (0.7 g), mp 226°–8° C. $[\alpha]^{26}_D$=+38° (1% in MeOH).

Analysis: $C_{17}H_{25}NO.HCl$ requires: C, 69.0; H, 8.9; N, 4.7 Found: C, 69.0; H, 9.0; H, 9.0; N, 4.5%

EXAMPLE 16

(1'R,3R,4aR,6R,8aR)-1,2,3,4,4a,5,6,7,8,8a-Decahydro-6-((4-methoxyphenyl)methyl)-(1'-phenylethyl)quinoline A). 4-Methoxybenzylcyclohexanone (43.68 g, 0.2 mol) was dissolved in toluene (250 ml). To this solution pyrrolidine (25 ml, 0.3 mol) was added together with a catalytic amount of p-toluenesulphonic acid. The reaction mixture was refluxed with a Dean and Stark apparatus for 20 hours. Once the predicted amount of water had been collected, the solvent was removed under vacuum. Excess pyrrolidine was removed by adding a little toluene and evaporating under reduced pressure. The resulting liquid was dissolved in methanol (200 ml) and to the resulting stirred solution, methyl acrylate (18 ml, 0.2 mol) dissolved in methanol (50 ml) was added dropwise. This was stirred for 20 hours at room temperature. The resulting liquid was neutralised with sodium bicarbonate and the product extracted into dichloromethane. The solution was then passed through a bed of florisil. The solvent was evaporated leaving an oil which was purified by distillation. 2-(2-Methoxycarbonylethyl)-4-(4-methoxybenzyl)cyclohexanone distilled at 155° C., 0.05 mmHg.

B). The ketone prepared in step (A) above (34 g, 112 mmol) was heated at reflux with R(+)-α-methylbenzylamine (14.8 g 122 mmol) and toluene (500 ml) in the presence of a catalytic amount of p-toluenesulphonic acid using a Dean and Stark water separator. After 24 hours the reaction mixture was concentrated in vacuo, dissolved in absolute ethanol and hydrogenated over Raney nickel under 50 psi hydrogen at room temperature. After 4 days the catalyst was filtered off and the filtrate concentrated in vacuo. The isomer mixture was separated by chromatography on a silica column using diisopropylether as eluent to give methyl (1'R,1S,2R,5R)-5-((4-methoxyphenyl)methyl)-2-(1'-phenylethylamino)ethylamino)cyclohexanepropionate (Rf 0.35).

C). The product of step (B) (10 g) was heated in toluene (200 ml) in the presence of acetic acid (2 ml) for 24 hours. After cooling the acetic acid was removed by washing with a saturated aqueous sodium bicarbonate solution. The organic phase was separated, dried ($Na_2SO_4$) and evaporated. The residue was chromatographed on a silica column using diisopropyl ether as eluent to give (+)-(1'R,4aS,6R,8aR)-3,4,4a,5,6,7,8,8a-octa-hydro-6-((4-methoxyphenyl)methyl)-1-(1'-phenylethyl)quinolin-2[1H]-one, mp 103°–4° C.

D). nBuLi (4.8 ml, 7.6 mmol) was added to (+)-bis [(R)-1-phenylethyl]amine, hydrochloride (1 g, 3.8 mmol) in THF (10 ml) at –20° C. and stirred for 15 minutes. (+)-(1'R,4aS,6R,8aR)-3,4,4a,5,6,7,8,8a-octahydro-6-((4-methoxyphenyl)methyl)-1-(1'-phenylethyl)quinolin-2[1H]-one (1.44 g 3.8 mol) (prepared according to step C) in THF (3 ml) was added at –50° C., stirred for 15 minutes then allowed to warm to room temperature and stirred for 2 hours. The resulting anion was cooled to –50° C. and treated with trimethylsilylethoxymethyl chloride (0.64 g, 3.82 mmol), stirred for 15 minutes then allowed to warm to room temperature and stirred for 1 hour.

The reaction mixture was quenched with 1M HCl, evaporated down and extracted into ethyl acetate. After drying ($Na_2SO_4$) and concentrating in vacuo a colourless oil was obtained. The starting material was removed by column chromatography on silica with ethyl acetate as eluent. Fractions containing the protected title compound were collected and evaporated to give a solid. This product (2 g, 3.9 mol) dichloromethane (20 ml) was treated with $BF_3.Et_2O$ (6 ml, 19 mol) at room temperature and stirred for 10 minutes.

The reaction mixture was partitioned between dichloromethane and saturated aqueous $NaHCO_3$ solution. An isomer mixture including (+)-(1'R,3S,4aR,6R,8aR)-3,4,4a,5,6,7,8,8a-octahydro-3-hydroxymethyl-6-((4-methoxyphenyl)methyl)-1-(1'-phenylethyl)quinolin-2(1H)-one was separated by column chromatography on silica-diisopropylether. This compound was further purified by recrystallisation from diisopropyl ether, mp 127°–8° C.

E) (+)-(1'R,3S,4aR,6R,8aR)-3,4,4a,5,6,7,8,8a-octahydro-3-hydroxymethyl-6-((4-methoxyphenyl)methyl)-1-(1'-phenylethyl)quinolin-2(1H)-one (500 mg, 1.23 mmol) in THF (5 ml) was treated with $BH_3DMS$ (0.37 ml, 3.7 mmol) and stirred under argon for 18 hours. The reaction was quenched with water, stirred for five minutes then acidified with acetic acid. After stirring for 30 minutes the organic solvent was evaporated, the remaining aqueous phase diluted with methanol and evaporated down again. The residue was basified with aqueous ammonia and extracted into diethyl ether, the organic phase separated, dried ($Na_2SO_4$) and concentrated in vacuo to give the title compound. This was purified by column chromatography (SiO2-diisopropylether) and converted to the hydrochloride salt in diethyl ether and recrystallised from ethyl acetate, mp 185°–187° C. $[\alpha]^{27}_D$=+22° (1% in MeOH).

Analysis: $C_{26}H_{35}NO_2.HCl$. 0.5 $H_2O$ requires: C, 71.1; H, 8.5; N, 3.2 Found: C, 71.1, H, 8.4; N, 3.3%.

EXAMPLE 17

(+)-(1'R,3R,4aR,6R,8aR)-3-Acetoxymethyl-1,2,3,4,4a,5,6,7,8,8a-decahydro-6-((4-methoxyphenyl)methyl)-1-(1'-phenylethyl)quinoline Also isolated by chromatography from the reaction of Example 16 was the title compound mp 79°–80° C. $[\alpha]^{27}_D$=+43° (1% $CHCl_3$).

EXAMPLE 18

(−)-(3R,4aR,6S,8aS)-1,2,3,4,4a,5,6,7,8,8a-Decahydro-3-hydroxymethyl-6-((4-methoxyphenyl)methyl)quinoline (−)-(1'S,3R,4aR,6S,8aS)-1,2,3,4,4a,5,6,7,8,8a-Decahydro-3-hydroxymethyl-6-((3-methoxyphenyl)methyl)-(1'-phenylethyl)quinoline (79.5 mg, 2.0 mmol, prepared according to Example 11) was hydrogenolysed in hexane:ethanol, 1:1 (100 ml) and glacial acetic acid (2 ml) over palladium hydroxide on carbon (150 mg) under hydrogen at 50 psi at room temperature for 18 hours. The mixture was filtered and concentrated in vacuo to give the title compound as an oil which was converted to the hydrochloride salt in ethereal HCl, (420 mg) mp 166°–168° C., HCl. $[\alpha]_D^{26}=+2°$ (1% in MeOH)

Analysis: $C_{18}H_{27}NO_2$. HCl requires: C, 66.4; H, 8.6; N, 4.3 Found: C, 65.9; H, 8.9; N, 4.2%.

EXAMPLE 19

(+)-(1'R,3S,4aS,6R,8aR)-1,2,3,4,4a,5,6,7,8,8a-Decahydro-3-hydroxymethyl-6-((4-methoxyphenyl)methyl)-1-(1'-phenylethyl)quinoline 4-Methoxybenzyltriphenylphosphonium bromide (44 g, 95 mmol) in toluene (1.251) was refluxed for 18 hours and water collected by Dean-Stark apparatus. Half of the toluene was distilled off and the suspension allowed to cool to room temperature. Tetrahydrofuran (THF) (600 ml) was added and the mixture cooled to −15° C. then treated with nBuLi (59 ml, 95 mmol) under argon. The solution was allowed to warm to 0° C. and was stirred for 2 hours.

B) (1'R,4aR,8aR)-3,4,4a,5,6,7,8,8a-Octahydro-1-(1'-phenylethyl)-1H-2,6,-dioxoquinoline (prepared by analogy with Example 14 step D using R(+)α-methylbenzylamine) previously dried by azeotroping with toluene, (25 g 92 mmol) in THF (200 ml) was added slowly to the anion produced in step A) keeping the temperature below 5° C. After stirring for 5 days the triphenylphosphine oxide formed was filtered off and washed with ethyl acetate. The filtrates were evaporated down yielding an oil, which crystallised from ethyl acetate. The mother liquors were filtered through a short pad of $SiO_2$ in ethyl acetate, and the filtrate chromatographed on $SiO_2$ in ethyl acetate—di-isopropyl ether (2:3), yielding two fractions. The faster running fraction was the Z isomer and the slower the E isomer. The E isomer (−)-(1'R,4aR,6E,8aR)-1,3,4,4a,5,7,8,8a-octahydro-6-((4-methoxyphenyl)methylidene)-1-(1'-phenylethyl)quinolin-2[1H]-one) crystallised from di-isopropyl ether and was collected, mp 92°–94°$[\alpha]_D^{26}=−181°$ (1% $CHCl_3$).

C). (1'R,4aR,6E,8aR)-1,3,4,4a,5,7,8,8a-Octahydro-6-((4-methoxyphenyl)-methylidene)-1-(1'-phenylethyl)quinolin-2[1H]-one (20 g 53 mmol) (prepared according to step B), was reduced by transfer hydrogenation over palladium black (1 g) in cyclohexene (200 ml) at reflux for 18 hours. The catalyst was filtered off and the filtrate concentrated in vacuo. The resulting oil was crystallised from diisopropyl ether and then recrystallised from the same solvent to give (−)-(1'R,4aR,6R,8aR)-3,4,4a,5,6,7,8,8a-octahydro-6-((4-methoxyphenyl)methyl-1-(1'-phenylethyl)quinoline-2[1H]-one, mp=130°–2° C.

D). (−)-(1'R,4aR,6R,8aR)-3,4,4a,5,6,8,8a-Octahydro-6-(4-methoxyphenyl)methyl-1-(1'-phenylethyl)quinoline-2[1H]-one, prepared according to Step C, (1 g, 2.7 mmol) in THF (5 ml) was added to LiTMP (1.85 ml, nBuLi, 0.39 g TMP, 2.8 mmol) in THF (10 ml) under Ar at −78° C. for 1½ hour and the resulting anion treated with trimethylsilylethoxymethyl chloride (0.49 g, 2.94 mmol). The reaction was allowed to warm to room temperature and stirred for 1 hour. The solvent was evaporated off and the residue partitioned between 2M HCl and ethyl acetate. The organic phase was separated, dried ($Na_2SO_4$) and concentrated in vacuo, yielding an oil (1.36 g). The oil (11.5 g, 22.8 mmol) in dichloromethane (100 ml) was treated at 0° C. under Ar, with $BF_3.OEt_2$ (35 ml, 2.8 mmol) and stirred for 15 minutes. The reaction was quenched with water, the organic phase separated and the aqueous extracted again with $CH_2Cl_2$. The combined $CH_2Cl_2$ layers were washed with saturated $NaHCO_3$ solution, dried ($Na_2SO_4$) and concentrated in vacuo to give 9.5 g of an oil. This was chromatographed ($SiO_2$-hexane/ethyl acetate (1:1)). The fractions containing (−)-(1'R,3R,4aS,6R,8aR)-3-hydroxymethyl-3,4,4a,5,6,7,8,8a-octahydro-6-(4-methoxyphenylmethyl)-1-(1'-phenylethyl)quinolin-2[1H]-one were collected, evaporated and the residue crystallised from di-isopropylether, mp 136°–7° C.

E). (−)-(1'R, 3R, 4aS, 6R, 8aR)-3-Hydroxymethyl-3,4,4a,5,6,7,8,8a-octahydro-6-((4-methoxyphenyl)methyl)-1-(1'-phenylethyl)quinolin-2[1H]-one (2.8 g 1.9 mmol, prepared according to step D, in THF (20 ml) was treated at room temperature under argon with 10M $BH_3$.DMS (2.06 ml, 2.06 mmol) and the reaction stirred for 4 hours. The resulting solution was cooled to 0° C. and treated with acetic acid (2 ml). After stirring for five minutes the reaction was diluted with water, extracted into ether and the organic phase was back extracted into 2M HCl. The combined aqueous phases were basified with ammonia and extracted twice into chloroform. The combined chloroform extracts were dried ($Na_2SO_4$), yielding 2.3 g of the title compound which was converted to the hydrochloride salt using ethereal HCl, mp 105–106, $[\alpha]_D^{27}=+13°$ (1% in MeOH).

Analysis: $C_{26}H_{35}NO_2$. HCl. 0.25$H_2O$ requires: C,71.9; H, 8.5; N, 3.2

Found: C, 71.8; H, 8.6; N, 3.1%.

We claim:

1. A compound of generic formula:

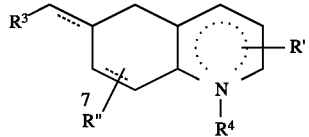

or a pharmaceutically acceptable salt thereof, where the dotted lines represent optional bonds with the nitrogen ring optional bonds being between one adjacent pair of ring atoms, $R^3$ is an optionally substituted $C_6$–$C_{10}$ aryl or heteroaryl group; said heteroaryl group containing 5 to 10 ring atoms of which one or more (e.g. up to 3) of said atoms are heteroatoms selected from oxygen, nitrogen and sulfur, the same or different; said aryl or heteroaryl radicals being optionally substituted by one or more substituents, the same or different, selected from $C_1$–$C_6$ alkyl; $C_1$–$C_6$ alkyl substituted by $C_6$–$C_{10}$ aryl or heteroaryl where heteroaryl is as defined above; $C_1$–$C_6$ alkoxy; $C_1$–$C_6$ alkoxy substituted by $C_6$–$C_{10}$ aryl or heteroaryl as defined above; halogen; halo $C_1$–$C_6$ alkyl; halo $C_1$–$C_6$ alkoxy; carboxy; hydroxy($C_1$–$C_6$)alkyl; ($C_1$–$C_6$alkoxy)carbonyl; amino including substituted amino, e.g. mono- or di- ($C_1$–$C_6$ alkyl)-amino; nitro; hydroxy; mercapto; $C_1$–$C_6$alkylthio; ($C_1$–$C_6$)alkyl carbonyl; ($C_6$–$C_{10}$aryl)carbonyl; ($C_2$–$C_7$)alkanoyloxy;

($C_7$–$C_{11}$)aroyloxy; ($C_1$–$C_6$)alkoxycarbonylamino; $C_6$–$C_{10}$ aryl) carbonylamino; ($C_2$–$C_7$) alkoxycarbonylamino; $C_6$–$C_{10}$ aryl; heteroaryl as defined above; and $C_1$–$C_2$ alkylenedioxy;

$R^4$ represents hydrogen, or a group of formula —$CR^aR^bR^c$ where $R^a$, $R^b$ and $R^c$ are independently selected from hydrogen, $C_1$–$C_6$ alkyl, optionally substituted $C_6$–$C_{10}$ aryl, optionally substituted heteroaryl, $C_1$–$C_6$ alkyl substituted by optionally substituted $C_6$–$C_{10}$ aryl or heteroaryl in which the substituent(s) is/are $C_1$–$C_6$ alkyl; $C_1$–$C_6$ alkyl substituted by $C_6$–$C_{10}$ aryl or heteroaryl where heteroaryl is as defined above; $C_1$–$C_6$ alkoxy; $C_1$–$C_6$ alkoxy substituted by $C_6$–$C_{10}$ aryl or heteroaryl where heteroaryl is as defined above; halogen; halo $C_1$–$C_6$ alkyl; halo $C_1$–$C_6$ alkoxy; carboxy; hydroxy($C_1$–$C_6$)alkyl; ($C_1$–$C_6$)alkoxy)carbonyl; amino including substituted amino, e.g. mono- di- ($C_1$–$C_6$ alkyl)-amino; nitro; hydroxy; mercapto; $C_1$–$C_6$alkylthio; ($C_1$–$C_6$)alkyl carbonyl; ($C_6$–$C_{10}$ aryl) carbonyl; ($C_2$–$C_7$)alkanoyloxy; ($C_7$–$C_{11}$)aroyloxy; ($C_1$–$C_6$)alkylcarbonylamino, ($C_6$–$C_{10}$aryl) carbonylamino; ($C_2$–$C_7$) alkoxycarbonylamino; $C_6$–$C_{10}$aryl; heteroaryl as defined above; and $C_1$–$C_2$ alkylenedioxy;

R' represents one or more optional substituents the same or different, selected from one or more of the following: halogen, $C_1$–$C_6$ alkyl, $C_2$–$C_7$ alkoxycarbonyl, $C_1$–$C_6$ hydroxyalkyl, CN, aminocarbonyl, $C_2$–$C_7$ alkanoyloxy ($C_1$–$C_6$)alkyl, carboxy, $C_2$–$C_7$ alkanoxyamino, optionally substituted $C_6$–$C_{10}$ aryl or heteroaryl or an optionally substituted ($C_6$–$C_{10}$ aryl)alkyl or a heteroaryl alkyl radical; said heteroaryl group containing 5 to 10 ring atoms of which one or more (e.g. up to 3) of said atoms are heteroatoms selected from oxygen, nitrogen and sulfur, the same or different; said aryl or heteroaryl radicals being optionally substituted by one or more substituents, the same or different, selected from $C_1$–$C_6$ alkyl; $C_1$–$C_6$ alkyl substituted by $C_6$–$C_{10}$ aryl or heteroaryl as defined above; $C_1$–$C_6$ alkoxy; $C_1$–$C_6$ alkoxy substituted by $C_6$–$C_{10}$ aryl or heteroaryl as defined above; halogen; halo $C_1$–$C_6$ alkyl, halo $C_1$–$C_6$ alkoxy; carboxy; hydroxy($C_1$–$C_6$)alkyl $C_2$–$C_7$ alkanoyloxy ($C_1$–$C_6$)alkyl; ($C_1$–$C_6$alkoxy)carbonyl; amino including substituted amino, e.g. mono- or di- ($C_1$–$C_6$ alkyl) -amino; nitro; hydroxy; mercapto; $C_1$–$C_6$alkylthio; ($C_1$–$C_6$alkyl)carbonyl; ($C_6$–$C_{10}$aryl)carbonyl; ($C_2$–$C_7$) alkanoyloxy; ($C_7$–$C_{11}$)aroyloxy; ($C_1$–$C_6$alkyl) carbonyl-amino, ($C_6$–$C_{10}$aryl)carbonylamino; ($C_2$–$C_7$ alkoxycarbonyl)amino; $C_6$–$C_{10}$ aryl; heteroaryl as defined above; and $C_1$–$C_2$ alkylenedioxy; and R" represents one or more optional mono- or di-valent substituents in the 5, 7 or 8 positions the same or different: monovalent substituents being selected from the following: $C_1$–$C_6$ alkyl, $C_2$–$C_7$ alkanoyloxy, hydroxy, amino, $C_2$–$C_7$ alkanoylamino, $C_1$–$C_6$alkylamino, $C_1$–$C_6$ hydroxyalkyl, R" can also represent hydroxy in the 6 position (when the optional bond is absent); the di-valent substituents being selected from oxo (i.e. =O) and methylene (i.e. =$CH_2$).

2. A compound according to claim 1 having the formula

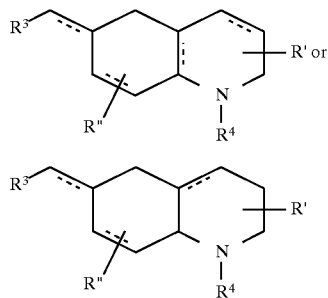

wherein

R' represents one or more optional substituents the same or different, selected from one or more of the following: halogen, $C_1$–$C_6$ alkyl, $C_2$–$C_7$alkoxycarbonyl, $C_1$–$C_6$ hydroxyalkyl, CN, aminocarbonyl, $C_2$–$C_7$ alkanoyloxy ($C_1$–$C_6$)alkyl, carboxy, $C_2$–$C_7$ alkanoxyamino, optionally substituted $C_6$–$C_{10}$ or heteroaryl or an optionally substituted ($C_6$–$C_{10}$ aryl)alkyl or a heteroaryl alkyl radical; said heteroaryl group containing 5 to 10 ring atoms of which one or more (e.g. up to 3) of said atoms are heteroatoms selected from oxygen, nitrogen and sulfur, the same or different; said aryl or heteroaryl radicals being optionally substituted by one or more substituents, the same or different, selected from $C_1$–$C_6$ alkyl; $C_1$–$C_6$ alkyl substituted by $C_6$–$C_{10}$ aryl or heteroaryl as defined above; $C_1$–$C_6$ alkoxy; $C_1$–$C_6$ alkoxy substituted by $C_6$–$C_{10}$ aryl or heteroaryl as defined above; halogen; halo $C_1$–$C_6$ alkyl, halo $C_1$–$C_6$ alkoxy; carboxy; hydroxy($C_1$–$C_6$)alkyl $C_2$–$C_7$ alkanoyloxy ($C_1$–$C_6$)alkyl; ($C_1$–$C_6$alkoxy)carbonyl; amino including substituted amino, e.g. mono- or di- ($C_1$–$C_6$ alkyl) -amino; nitro; hydroxy; mercapto; $C_1$–$C_6$alkylthio; ($C_1$–$C_6$alkyl)carbonyl; ($C_6$–$C_{10}$aryl)carbonyl; ($C_2$–$C_7$) alkanoyloxy; ($C_7$–$C_{11}$)aroyloxy; ($C_1$–$C_6$alkyl) carbonylamino, ($C_6$–$C_{10}$aryl)carbonylamino; ($C_2$–$C_7$ alkoxycarbonyl)amino; $C_6$–$C_{10}$aryl; heteroaryl as defined above; and $C_1$–$C_2$ alkylenedioxy; and R" represents one or more optional mono- or di-valent substituents in the 5, 7 or 8 positions the same or different: monovalent substituents being selected from the following: $C_1$–$C_6$ alkyl, $C_2$–$C_7$ alkanoyloxy, hydroxy, amino, $C_2$–$C_7$ alkanoylamino, $C_1$–$C_6$alkylamino, $C_1$–$C_6$ hydroxyalkyl, R" can also represent hydroxy in the 6 position (when the optional bond is absent); the di-valent substituents being selected from oxo (i.e. =O) and methylene (i.e. =$CH_2$).

$R^3$ is an optionally substituted $C_6$–$C_{10}$ aryl or heteroaryl group; said heteroaryl group containing 5 to 10 ring atoms of which one or more (e.g. up to 3) of said atoms are heteroatoms selected from oxygen, nitrogen and sulfur, the same or different; said aryl or heteroaryl radicals being optionally substituted by one or more substituents the same or different, selected from: $C_1$–$C_6$ alkyl; $C_1$–$C_6$ alkyl substituted by $C_6$–$C_{10}$ aryl or heteroaryl as defined above; $C_1$–$C_6$ alkoxy; $C_1$–$C_6$ alkoxy substituted by $C_6$–$C_{10}$ aryl or heteroaryl as defined above; halogen; halo $C_1$–$C_6$ alkyl; halo $C_1$–$C_6$ alkoxy; carboxy; hydroxy($C_1$–$C_6$)alkyl; ($C_1$–$C_6$alkoxy) carbonyl; amino including substituted amino, e.g. mono- or di- ($C_1$–$C_6$ alkyl)-amino; nitro; hydroxy; mercapto; $C_1$–$C_6$alkylthio; ($C_1$–$C_6$)alkyl carbonyl;

($C_6$–$C_{10}$ aryl)carbonyl; ($C_2$–$C_7$)alkanoyloxy; ($C_7$–$C_{11}$) aroyloxy; ($C_1$–$C_6$)alkylcarbonylamino, ($C_6$–$C_{10}$aryl)carbonylamino; ($C_2$–$C_7$) alkoxycarbonylamino; $C_6$–$C_{10}$ aryl; heteroaryl as defined above; and $C_1$–$C_2$ alkylenedioxy;

$R^4$ represents hydrogen, or a group of formula —$CR^aR^bR^c$ where $R^a$, $R^b$ and $R^c$ are independently selected from hydrogen, $C_1$–$C_6$ alkyl, optionally substituted $C_6$–$C_{10}$ aryl, optionally substituted heteroaryl, $C_1$–$C_6$ alkyl substituted by optionally substituted $C_6$–$C_{10}$ aryl or heteroaryl in which the substituent(s) is/are for example as illustrated above in connection with $R^3$;

and the dotted lines represent optional bonds.

3. A compound of claim 1 which is 1,2,3,4,4a,5,6,7,8,8a-decahydro-3-hydroxymethyl-6-((4-methoxyphenyl)methyl)- quinoline or a pharmaceutically acceptable salt thereof.

4. A compound of claim 1 which is 1,2,3,4,4a,5,6,7,8,8a-decahydro-6-((4-methoxyphenyl)methyl)-1-(1'-phenylethyl)quinoline or a pharmaceutically acceptable salt thereof.

5. A compound of claim 1 which is 1,2,3,4,4a,5,6,7,8,8a-decahydro-3-hydroxymethyl-6-((4-methoxyphenyl)methyl)-(1'-phenylethyl)quinoline or a pharmaceutically acceptable salt thereof.

6. A compound of claim 1 which is 3,4,4a,5,6,7,8,8a-octahydro-6-((4-methoxyphenyl)methyl)quinoline or a pharmaceutically acceptable salt thereof.

7. A compound of claim 1 which is 1,2,3,4,4a,5,6,7,8,8a-decahydro-6-((4-methoxyphenyl)-methyl -3-methyl-1-(1'-phenylethyl)quinoline or a pharmaceutically acceptable salt thereof.

8. A compound of claim 1 which is 3-acetoxymethyl-1,2,3,4,4a,5,6,7,8,8a-decahydro-6-((4-methoxyphenyl)methyl)-1-(1'-phenylethyl)quinoline or a pharmaceutically acceptable salt thereof.

9. A compound of claim 1 which is:

(±)-(3SR,4aSR,6RS,8aRS)-1,2,3,4,4a,5,6,7,8,8a-decahydro-3-hydroxymethyl-6-((4-methoxyphenyl)methyl)quinoline;

(±)-(3RS,4aRS,6SR,8aSR)-1,2,3,4,4a,5,6,7,8,8a-decahydro-3-hydroxymethyl-6-((4-methoxyphenyl)methyl)quinoline;

(±)-(3RS,4aRS,6SR,8aRS)-1,2,3,4,4a,5,6,7,8,8a-decahydro-3-hydroxymethyl-6-((4-methoxyphenyl)methyl)quinoline;

(−)-(3S,4aR,6S,8aS)-1,2,3,4,4a,5,6,7,8,8a-decahydro-3-hydroxymethyl-6-((4-methoxyphenyl)methyl)quinoline;

(+)-(3R,4aS,6R,8aR)-1,2,3,4,4a,5,6,7,8,8a-decahydro-3-hydroxymethyl-6-((4-methoxyphenyl)methyl)quinoline;

(+)-(1'R,4aS,6R,8aR)-1,2,3,4,4a,5,6,7,8,8a-decahydro-6-((4-methoxyphenyl)methyl-1-(1'-phenylethyl)quinoline;

(+)-(1'R,4aS,6S,8aR)-1,2,3,4,4a,5,6,7,8,8a-decahydro-6-((4-methoxyphenyl)methyl)-1-(1'-phenylethyl)quinoline;

(−)-(4aS,6S,8aR)-3,4,4a,5,6,7,8,8a-decahydro-6-((4-methoxyphenyl)methyl)quinoline;

(−)-(1'R,3R,4aR,6S,8aR)-1,2,3,4,4a,5,6,7,8,8a-decahydro-3-hydroxymethyl-6-((4-methoxyphenyl)methyl)-(1'-phenylethyl)quinoline;

(−)-(1'S,3R,4aR,6S,8aS)-1,2,3,4,4a,5,6,7,8,8a-decahydro-3-hydroxymethyl-6-((4-methoxyphenyl)methyl)-(1'-phenylethyl)quinoline;

(+)-(3S,4aS,6R,8aR)-1,2,3,4,4a,5,6,7,8,8a-decahydro-3-hydroxymethyl-6-((4-methoxyphenyl)methyl)quinoline;

(−)-(1'R,3R,4aR,6S,8aR)-1,2,3,4,4a,5,6,7,8,8a-decahydro-6-((4-methoxyphenyl)methyl)-3-methyl-1-(1'-phenylethyl)quinoline;

(−)-(1'S,4aS,6R,8aS)-1,2,3,4,4a,5,6,7,8,8a-decahydro-6-((4-methoxyphenyl)methyl)-1-(1'-phenylethyl)quinoline;

(+)(4aR,6R,8aS)-1,2,3,4,4a,5,6,7,8,8a-decahydro-6-((4-methoxyphenyl)methyl)quinoline;

(1'R,3R,4aR,6R,8aR)-1,2,3,4,4a,5,6,7,8,8a-decahydro-6-((4-methoxyphenyl)methyl)-(1'-phenylethyl)quinoline;

(+)-(1'R,3R,4aR,6R,8aR)-3-acetoxymethyl-1,2,3,4,4a,5,6,7,8,8a-decahydro-6-((4-methoxyphenyl)methyl)-1-(1'-phenylethyl)quinoline;

(−)-(3R,4aR,6S,8aS)-1,2,3,4,4a,5,6,7,8,8a-decahydro-3-hydroxymethyl-6-((4-methoxyphenyl)methyl)quinoline;

(+)-(1'R,3S,4aS,6R,8aR)-1,2,3,4,4a,5,6,7,8,8a-decahydro-3-hydroxymethyl-6-((4-methoxyphenyl)methyl)-1-(1'-phenylethyl)quinoline.

10. A compound having the formula

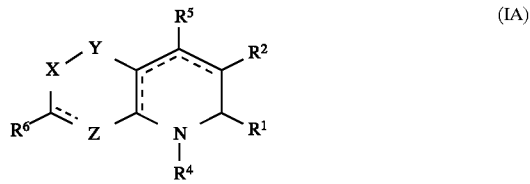

(IA)

or a pharmaceutically acceptable salt thereof, wherein the dotted lines represent optional bonds with the nitrogen ring optional bond being between one adjacent pair of ring atoms in the 3, 4; 4, 4a; or 4a, 8a positions;

$R^1$ is H, $C_1$–$C_6$ alkyl, optionally substituted $C_6$–$C_{10}$ aryl, optionally substituted heteroaryl or an optionally substituted ($C_6$–$C_{10}$ aryl)alkyl or heteroarylalkyl radical; said heteroaryl group containing 5 to 10 ring atoms of which one or more of said atoms are heteroatoms selected from oxygen, nitrogen and sulfur, the same or different; said aryl or heteroaryl radicals being optionally substituted by one or more substituents the same or different selected from $C_1$–$C_6$ alkyl; $C_1$–$C_6$ alkyl substituted by $C_6$–$C_{10}$ aryl or heteroaryl as defined above; $C_1$–$C_6$ alkyl alkoxy substituted by $C_6$–$C_{10}$ aryl or heteroaryl as defined above; halogen; halo $C_1$–$C_6$ alkyl; halo $C_1$–$C_6$ alkoxy; carboxy; hydroxy($C_1$–$C_6$)alkyl; ($C_1$–$C_6$alkoxy)carbonyl; amino including substituted amino, e.g. mono- or di- ($C_1$–$C_6$ alkyl)-amino; nitro; hydroxy; mercapto; $C_1$–$C_6$alkylthio; ($C_1$–$C_6$alkyl) carbonyl; ($C_6$–$C_{10}$ aryl)carbonyl; ($C_2$–$C_7$)alkanoyloxy; ($C_7$–$C_{11}$)aroyloxy; ($C_1$–$C_6$)alkylcarbonylamino, ($C_6$–$C_{10}$aryl)carbonylamino; ($C_2$–$C_7$) alkoxycarbonylamino; or $C_6$–$C_{10}$ aryl; or heteroaryl as defined above;

$R^2$ is hydrogen, $C_1$–$C_6$ alkyl, $C_1$–$C_6$ hydroxyalkyl, $C_2$–$C_7$ alkanoyloxy($C_1$–$C_6$)alkyl, ($C_1$–$C_6$ alkoxy)carbonyl, cyano, aminocarbonyl, carboxy or $C_2$–$C_7$ alkanoylamino;

X is a group of formula

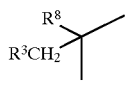 (vii)

or

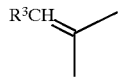 (viii)

where $R^8$ is H or OH;

$R^3$ is a $C_6$–$C_{10}$ aryl or a heteroaryl radical containing 5 to 10 ring atoms of which one or more (e.g. up to 3) of said atoms are heteroatoms selected from oxygen, nitrogen and sulfur, the same or different; said aryl or heteroaryl radical being optionally substituted by one or more substituents the same or different selected from $C_1$–$C_6$ alkyl; $C_1$–$C_6$ alkyl substituted by $C_6$–$C_{10}$ aryl or heteroaryl as defined above; $C_1$–$C_6$ alkoxy; $C_1$–$C_6$ alkoxy substituted by $C_6$–$C_{10}$ aryl or heteroaryl as defined above; halogen; halo $C_1$–$C_6$ alkyl; halo $C_1$–$C_6$ alkoxy; carboxy; hydroxy($C_1$–$C_6$)alkyl; ($C_1$–$C_6$alkoxy)carbonyl; amino including substituted amino, e.g. mono- or di- ($C_1$–$C_6$ alkyl)-amino; nitro; hydroxy; mercapto; $C_1$–$C_6$alkylthio; ($C_1$–$C_6$alkyl) carbonyl; ($C_6$–$C_{10}$ aryl)carbonyl; ($C_2$–$C_7$)alkanoyloxy; ($C_7$–$C_{11}$) aroyloxy; ($C_1$–$C_6$)alkylcarbonylamino, ($C_6$–$C_{10}$aryl)carbonylamino; ($C_2$–$C_7$) alkoxycarbonylamino; or $C_6$–$C_{10}$ aryl; and heteroaryl as defined above;

Y is

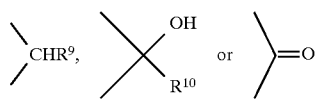

where $R^9$ represents hydrogen, $C_1$–$C_6$ alkyl, $C_2$–$C_7$ alkanoyloxy, optionally substituted heteroaryl, optionally substituted $C_6$–$C_{10}$ aryl or $CH_2OH$; and $R^{10}$ represents hydrogen or $C_1$–$C_6$ alkyl;

and $R^4$ represents hydrogen, or a group of formula —$CR^aR^bR^c$ where $R^a$, $R^b$ and $R^c$ are independently selected from hydrogen, $C_1$–$C_6$ alkyl, optionally substituted $C_6$–$C_{10}$ aryl, optionally substituted heteroaryl, $C_1$–$C_6$ alkyl substituted by optionally substituted $C_6$–$C_{10}$ aryl or optionally substituted heteroaryl in which the substituent(s), same or different, are selected from $C_1$–$C_6$ alkyl; $C_1$–$C_6$ alkyl substituted by $C_6$–$C_{10}$ aryl or heteroaryl as defined above; $C_1$–$C_6$ alkoxy; $C_1$–$C_6$ alkoxy substituted by $C_6$–$C_{10}$ aryl or heteroaryl as defined above; halogen; halo $C_1$–$C_6$ alkyl; halo $C_1$–$C_6$ alkoxy; carboxy; hydroxy($C_1$–$C_6$alkyl; ($C_1$–$C_6$alkoxy)carbonyl; amino including substituted amino, e.g. mono- or di- ($C_1$–$C_6$ alkyl)-amino; nitro; hydroxy; mercapto; $C_1$–$C_6$alkylthio; ($C_1$–$C_6$alkyl) carbonyl; ($C_6$–$C_{10}$ aryl)carbonyl; ($C_2$–$C_7$)alkanoyloxy; ($C_7$–$C_{11}$)aroyloxy; ($C_1$–$C_6$)alkylcarbonylamino, ($C_6$–$C_{10}$aryl)carbonylamino; ($C_2$–$C_7$) alkoxycarbonylamino; or $C_6$–$C_{10}$ aryl; or heteroaryl as defined above;

Z is C=O, C=$CH_2$, —$CHR^7$— or =C($R^7$)— where $R^7$ is hydrogen, OH, $CH_2OH$, $NH_2$, $C_2$–$C_7$ alkanoyloxy, $C_2$–$C_7$ alkanoylamino $C_1$–$C_6$alkylamino or a $C_1$–$C_6$ alkyl group optionally substituted by a $C_6$–$C_{10}$ aryl or heteroaryl as defined above; and $R^5$ is hydrogen, $C_1$–$C_6$ alkyl, $C_6$–$C_{10}$ aryl, heteroaryl or a $C_1$–$C_6$alkyl substituted by $C_6$–$C_{10}$ aryl or heteroaryl; said aryl or heteroaryl groups being optionally substituted by $C_1$–$C_6$ alkyl; $C_1$–$C_6$ alkyl substituted by $C_6$–$C_{10}$ aryl or heteroaryl as defined above; $C_1$–$C_6$ alkoxy; $C_1$–$C_6$ alkoxy substituted by $C_6$–$C_{10}$ aryl or heteroaryl as defined above; halogen; halo $C_1$–$C_6$ alkyl; halo $C_1$–$C_6$ alkoxy; carboxy; hydroxy($C_1$–$C_6$)alkyl; ($C_1$–$C_6$alkoxy)carbonyl; amino including substituted amino, e.g. mono- or di- ($C_1$–$C_6$ alkyl)-amino; nitro; hydroxy; mercapto; $C_1$–$C_6$alkylthio; ($C_1$–$C_6$alkyl) carbonyl; ($C_6$–$C_{10}$ aryl)carbonyl; ($C_2$–$C_7$)alkanoyloxy; ($C_7$–$C_{11}$)aroyloxy; ($C_1$–$C_6$)alkylcarbonylamino, ($C_6$–$C_{10}$aryl)carbonylamino; ($C_2$–$C_7$) alkoxycarbonylamino; or $C_6$–$C_{10}$ aryl; or heteroaryl as defined above; and $R^6$ is $NH_2$, $C_7$–$C_{17}$ aralkanoylamino, $C_2$–$C_7$ alkanoylamino or $R^6$ is one of the values listed for $R^5$ above.

11. A compound as claimed in claim 10 wherein X has formula (vii) wherein $R^8$ is hydrogen.

12. A compound as claimed in claim 10 wherein Y is $CH_2$.

13. A compound as claimed in claim 10 wherein Z is $CH_2$.

14. A compound as claimed in claim 10 wherein $R^1$, $R^5$ and $R^6$ are hydrogen.

15. A compound as claimed in claim 10 wherein $R^2$ is hydrogen, $C_1$–$C_6$ alkyl, $C_2$–$C_7$ alkoxycarbonyl, $C_2$–$C_7$ alkanoylamino, CN or $CN_2OH$.

16. A compound which has formula (K):

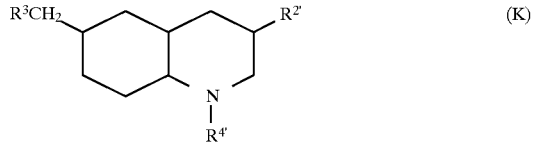 (K)

in which formula $R^{2'}$ is hydrogen, $C_1$–$C_6$ alkyl, $C_2$–$C_7$ alkoxycarbonyl, acetylamino, CN or $CH_2OH$;

$R^3$ is an optionally substituted $C_6$–$C_{10}$ aryl or heteroaryl group; said heteroaryl group containing 5 to 10 ring atoms of which one or more (e.g. up to 3) of said atoms are heteroatoms selected from oxygen, nitrogen and sulfur, the same or different; said aryl or heteroaryl radicals being optionally substituted by one or more substituents the same or different, selected from:

$C_1$–$C_6$ alkyl; $C_1$–$C_6$ alkyl substituted by $C_6$–$C_{10}$ aryl or heteroaryl as defined above; $C_1$–$C_6$ alkoxy; $C_1$–$C_6$ alkoxy substituted by $C_6$–$C_{10}$ aryl or heteroaryl as defined above; halogen; halo $C_1$–$C_6$ alkyl; halo $C_1$–$C_6$ alkoxy; carboxy; hydroxy($C_1$–$C_6$)alkyl; ($C_1$–$C_6$alkoxy)carbonyl; amino including substituted amino, e.g. mono- or di- ($C_1$–$C_6$ alkyl)-amino; nitro; hydroxy; mercapto; $C_1$–$C_6$alkylthio; ($C_1$–$C_6$)alkyl carbonyl; ($C_6$–$C_{10}$ aryl)carbonyl; ($C_2$–$C_7$) alkanoyloxy; ($C_7$–$C_{11}$)aroyloxy; ($C_1$–$C_6$) alkylcarbonylamino, ($C_6$–$C_{10}$aryl)carbonylamino; ($C_2$–$C_7$)alkoxycarbonylamino; $C_6$–$C_{10}$ aryl; heteroaryl as defined above; and $C_1$–$C_2$ alkylenedioxy;

and $R^{4'}$ is hydrogen, alkyl or optionally substituted aryl ($C_1$–$C_6$) alkyl in which the alkyl group is itself optionally substituted by $C_1$–$C_6$ alkyl.

17. A compound as claimed in claim 16 wherein $R^{2'}$ is hydrogen, $C_1$–$C_6$ alkyl, $C_2$–$C_7$ alkoxycarbonyl, $C_2$–$C_7$ alkanoylamino, CN or $CH_2OH$.

18. A compound as claimed in claim 16 wherein $R^3$ is substituted or unsubstituted phenyl wherein the substituent(s) is/are selected from one or more of the following the same or different: $C_1$–$C_6$ alkyl, $C_1$–$C_6$ alkoxy, hydroxy, halogen and methylene- or ethylene-dioxy.

19. A pharmaceutical composition comprising a compound of formula I

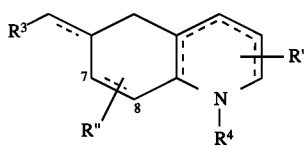

or a pharmaceutically acceptable salt thereof where the dotted lines represent optional bonds with the nitrogen ring optional bonds being between one adjacent pair or ring atoms.

$R^3$ is an optionally substituted $C_6$–$C_{10}$ aryl or heteroaryl group; said heteroaryl group containing 5 to 10 ring atoms of which one or more (e.g. up to 3) of said atoms are heteroatoms selected from oxygen, nitrogen and sulfur, the same or different; said aryl or heteroaryl radicals being optionally substituted by one or more substituents the same or different, selected from: $C_1$–$C_6$ alkyl; $C_1$–$C_6$ alkyl substituted by $C_6$–$C_{10}$ aryl or heteroaryl as defined above; $C_1$–$C_6$ alkoxy; $C_1$–$C_6$ alkoxy substituted by $C_6$–$C_{10}$ aryl or heteroaryl as defined above; halogen; halo $C_1$–$C_6$ alkyl; halo $C_1$–$C_6$ alkoxy; carboxy; hydroxy($C_1$–$C_6$)alkyl; ($C_1$–$C_6$alkoxy) carbonyl; amino including substituted amino, e.g. mono- or di- ($C_1$–$C_6$ alkyl)-amino; nitro; hydroxy; mercapto; $C_1$–$C_6$alkylthio; ($C_1$–$C_6$)alkyl carbonyl; ($C_6$–$C_{10}$ aryl)carbonyl; ($C_2$–$C_7$) alkanoyloxy; ($C_7$–$C_{11}$) aroyloxy; ($C_1$–$C_6$)alkylcarbonylamino, ($C_6$–$C_{10}$aryl) carbonylamino; ($C_2$–$C_7$) alkoxycarbonylamino; $C_6$–$C_{10}$ aryl; heteroaryl as defined above; and $C_1$–$C_2$ alkylenedioxy;

$R^4$ represents hydrogen, or a group of formula —$CR^aR^bR^c$ where $R^a$, $R^b$ and $R^c$ are independently selected from hydrogen, $C_1$–$C_6$ alkyl, optionally substituted $C_6$–$C_{10}$ aryl, optionally substituted heteroaryl, $C_1$–$C_6$ alkyl substituted by optionally substituted $C_6$–$C_{10}$ aryl or heteroaryl in which the substituent(s) is/are $C_1$–$C_6$ alkyl; $C_1$–$C_6$ alkyl substituted by $C_6$–$C_{10}$ aryl or heteroaryl as defined above; $C_1$–$C_6$ alkoxy; $C_1$–$C_6$ alkoxy substituted by $C_6$–$C_{10}$ aryl or heteroaryl as defined above; halogen; halo $C_1$–$C_6$ alkyl; halo $C_1$–$C_6$ alkoxy; carboxy; hydroxy($C_1$–$C_6$)alkyl; ($C_1$–$C_6$alkoxy)carbonyl; amino including substituted amino, e.g. mono- or di- ($C_1$–$C_6$ alkyl)-amino; nitro; hydroxy; mercapto; $C_1$–$C_6$alkylthio; ($C_1$–$C_6$)alkyl carbonyl; ($C_6$–$C_{10}$ aryl)carbonyl; ($C_2$–$C_7$)alkanoyloxy; ($C_7$–$C_{11}$)aroyloxy; ($C_1$–$C_6$alkylcarbonylamino, ($C_6$–$C_{10}$aryl)carbonylamino; ($C_2$–$C_7$) alkoxycarbonylamino; $C_6$–$C_{10}$ aryl; heteroaryl as defined above; and $C_1$–$C_2$ alkylenedioxy;

R' represents one or more optional substituents the same or different, selected from one or more of the following: halogen, $C_1$–$C_6$ alkyl, $C_2$–$C_7$ alkoxycarbonyl, $C_1$–$C_6$ hydroxyalkyl, CN, aminocarbonyl, $C_2$–$C_7$ alkanoyloxy ($C_1$–$C_6$)alkyl, carboxy, $C_2$–$C_7$ alkanoxyamino, optionally substituted $C_6$–$C_{10}$ or heteroaryl or an optionally substituted ($C_6$–$C_{10}$ aryl)alkyl or a heteroaryl alkyl radical; said heteroaryl group containing 5 to 10 ring atoms of which one or more (e.g. up to 3) of said atoms are heteroatoms selected from oxygen, nitrogen and sulfur, the same or different; said aryl or heteroaryl radicals being optionally substituted by one or more substituents the same or different, selected from: $C_1$–$C_6$ alkyl, $C_1$–$C_6$ alkoxy, or such groups substituted by $C_6$–$C_{10}$ aryl or heteroaryl as defined above; halogen; halo $C_1$–$C_6$ alkyl, halo $C_1$–$C_6$ alkoxy; carboxy; hydroxy($C_1$–$C_6$)alkyl $C_2$–$C_7$ alkanoyloxy($C_1$–$C_6$) alkyl; ($C_1$–$C_6$alkoxy)carbonyl; amino including substituted amino, e.g. mono- or di- ($C_1$–$C_6$ alkyl)-amino; nitro; hydroxy; mercapto; $C_1$–$C_6$alkylthio; ($C_1$–$C_6$alkyl)carbonyl; ($C_6$–$C_{10}$ aryl)carbonyl; ($C_2$–$C_7$) alkanoyloxy; ($C_7$–$C_{11}$)aroyloxy; ($C_1$–$C_6$alkyl) carbonylamino, ($C_6$–$C_{10}$aryl)carbonylamino; ($C_2$–$C_7$ alkoxycarbonyl)amino; $C_6$–$C_{10}$ aryl; heteroaryl as defined above; or $C_1$–$C_2$ alkylenedioxy; and R" represents one or more optional mono- or di-valent substituents in the 5, 7 or 8 positions the same or different: monovalent substituents being selected from the following: $C_1$–$C_6$ alkyl, $C_2$–$C_7$ alkanoyloxy, hydroxy, amino, $C_2$–$C_7$ alkanoylamino, $C_1$–$C_6$alkylamino, $C_1$–$C_6$ hydroxyalkyl, R" can also represent hydrogen in the 6 position (when the optional bond is absent); the di-valent substituents being selected from oxo (i.e. =O) and methylene (i.e. =$CH_2$);

and a pharmaceutically acceptable carrier.

* * * * *